(12) United States Patent
Shiota et al.

(10) Patent No.: US 10,322,989 B2
(45) Date of Patent: Jun. 18, 2019

(54) TRANSPARENT BODY PRODUCTION METHOD, TRANSPARENT BODY, AND AMORPHOUS BODY

(71) Applicant: TOKYO OHKA KOGYO CO., LTD., Kawasaki-shi (JP)

(72) Inventors: Dai Shiota, Kawasaki (JP); Kunihiro Noda, Kawasaki (JP); Hiroki Chisaka, Kawasaki (JP); Mayumi Kuroko, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

(21) Appl. No.: 15/509,168

(22) PCT Filed: Sep. 25, 2015

(86) PCT No.: PCT/JP2015/077158
§ 371 (c)(1),
(2) Date: Mar. 6, 2017

(87) PCT Pub. No.: WO2016/047766
PCT Pub. Date: Mar. 31, 2016

(65) Prior Publication Data
US 2017/0275223 A1    Sep. 28, 2017

(30) Foreign Application Priority Data

Sep. 26, 2014  (JP) ................. 2014-197423

(51) Int. Cl.
| | | |
|---|---|---|
| *C07C 43/215* | (2006.01) | |
| *C08F 20/30* | (2006.01) | |
| *C08F 16/32* | (2006.01) | |
| *C08F 20/20* | (2006.01) | |
| *C07C 43/23* | (2006.01) | |
| *C08F 16/26* | (2006.01) | |
| *C08F 216/12* | (2006.01) | |
| *C08F 216/14* | (2006.01) | |
| *C08F 220/30* | (2006.01) | |
| *C08F 220/32* | (2006.01) | |
| *C08F 222/10* | (2006.01) | |

(52) U.S. Cl.
CPC ............ *C07C 43/215* (2013.01); *C07C 43/23* (2013.01); *C08F 16/26* (2013.01); *C08F 16/32* (2013.01); *C08F 20/20* (2013.01); *C08F 20/30* (2013.01); *C08F 216/125* (2013.01); *C08F 216/14* (2013.01); *C08F 216/1416* (2013.01); *C08F 220/30* (2013.01); *C08F 220/32* (2013.01); *C08F 222/1006* (2013.01); *C08F 2216/145* (2013.01); *C08F 2216/1425* (2013.01); *C08F 2216/1433* (2013.01); *C08F 2216/1441* (2013.01); *C08F 2220/301* (2013.01); *C08F 2220/302* (2013.01); *C08F 2220/303* (2013.01); *C08F 2220/306* (2013.01); *C08F 2220/307* (2013.01); *C08F 2220/308* (2013.01); *C08F 2220/325* (2013.01); *C08F 2222/102* (2013.01)

(58) Field of Classification Search
CPC ....... C07C 43/215; C07C 43/23; C08F 20/30; C08F 16/32; C08F 20/20; C08F 16/26
See application file for complete search history.

(56) References Cited

U.S. PATENT DOCUMENTS

| | | | |
|---|---|---|---|
| 2008/0114100 A1* | 5/2008 | Hatsuda ................ | C08F 220/30 524/81 |
| 2013/0004676 A1 | 1/2013 | Ha | |
| 2016/0046551 A1 | 2/2016 | Shiota et al. | |
| 2016/0046552 A1 | 2/2016 | Shiota et al. | |
| 2016/0046742 A1 | 2/2016 | Shiota et al. | |

FOREIGN PATENT DOCUMENTS

| | | | | |
|---|---|---|---|---|
| JP | H04-325508 | | 11/1992 | |
| JP | 2004035821 A | * | 2/2004 | |
| JP | 2006-152115 A | | 6/2006 | |
| JP | 2011-201791 | | 10/2011 | |
| JP | 2011225644 A | * | 11/2011 | ........... C07C 43/215 |
| JP | 2014-034596 A | | 2/2014 | |
| JP | 2015-091774 A | | 5/2015 | |
| JP | 2015-091775 | | 5/2015 | |
| JP | 2015-151408 | | 8/2015 | |
| KR | 10-2014-0049584 A | | 4/2014 | |
| TW | 201527264 A | | 7/2015 | |
| WO | WO 2012/020659 | | 2/2012 | |
| WO | WO 2013/018302 | | 2/2013 | |
| WO | WO 2014/157674 | | 10/2014 | |
| WO | WO 2014/157675 | | 10/2014 | |
| WO | WO 2014/157676 | | 10/2014 | |

OTHER PUBLICATIONS

Extended European search report in European Patent Application No. 15843289.8, dated Aug. 7, 2017.

* cited by examiner

*Primary Examiner* — Rosalynd A Keys
(74) *Attorney, Agent, or Firm* — Knobbe, Martens, Olson & Bear LLP

(57) ABSTRACT

A transparent body production method that includes subjecting the compound represented by formula (1) to heating at a temperature equal to or greater than the melting point of said compound. In formula (1), each of $W^1$ and $W^2$ is the group represented by formula (2) in which the ring Z is an aromatic hydrocarbon ring, X is a single bond or —S—, $R^1$ is a single bond or an alkylene group having 1-4 carbon atoms, $R^2$ is a specific substituent, and m is an integer of 0 or higher, the group represented by formula (4) is —OH— or a (meth)acryloyloxy group, each of the rings $Y^1$ and $Y^2$ is an aromatic hydrocarbon ring, R is a single bond or a specific divalent group, each of $R^{3a}$ and $R^{3b}$ is —CN, a halogen group, or a monovalent hydrocarbon group, and each of n1 and n2 is an integer of 0-4.

16 Claims, 2 Drawing Sheets

TRANSPARENT BODY PRODUCTION METHOD, TRANSPARENT BODY, AND AMORPHOUS BODY

This application is the U.S. National Phase under 35 U.S.C. § 371 of International Application PCT/JP2015/077158, filed Sep. 25, 2015, designating the U.S., and published in Japanese as WO 2016/047766 on Mar. 31, 2016, which claims priority to Japanese Patent Application No. 2014-197423, filed Sep. 26, 2014, the entire contents of which are incorporated herein by reference.

TECHNICAL FIELD

The present invention relates to a transparent body production method using a vinyl-group-containing compound, and a transparent body obtained by this production method.

BACKGROUND ART

Fused polycyclic compounds have various excellent functions and have been used in various applications. For example, compounds having a fluorene skeleton (for example, 9,9-bisphenylfluorene skeleton) that are fused polycyclic aromatic compounds are known to have excellent functions in terms of optical properties such as light transmittance and refractive index and thermal properties such as heat resistance. Therefore, compounds having a fluorene skeleton are used as raw materials for optical members such as lenses, prisms, filters, image display materials, optical disk substrates, optical fibers, optical waveguides, casing materials, films, and coating materials. Examples of such compounds having a fluorene skeleton may include compounds disclosed in Patent Document 1.

Patent Document 1: Japanese Unexamined Patent Application, Publication No. 2011-201791

DISCLOSURE OF THE INVENTION

Problems to be Solved by the Invention

An object of the present invention is to provide a transparent body production method using a novel vinyl-group-containing compound, and a transparent body obtained by this production method.

Means for Solving the Problems

The present inventors have made extensive and intensive studies with a view to solving the above problems. As a result, the present inventors have found a transparent body production method using a novel vinyl-group-containing compounds, leading to the completion of the present invention. Specifically, the present invention provides the following matters.

According to a first aspect of the present invention, there is provided a method for producing a transparent body, in which the method includes heating a vinyl-group-containing compound at or above a melting point of the compound, and the compound is represented by the following general formula (1):

[Chem. 1]

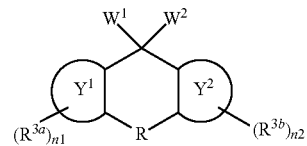

(1)

in which $W^1$ and $W^2$ each independently represent a group represented by the following general formula (2), a group represented by the following general formula (4), a hydroxyl group, or a (meth)acryloyloxy group, provided that $W^1$ and $W^2$ do not simultaneously represent a hydroxyl group or the group represented by the following general formula (4); a ring $Y^1$ and a ring $Y^2$ represent an aromatic hydrocarbon ring which may be the same or different; R represents a single bond, an optionally substituted methylene group, an ethylene group that is optionally substituted and may contain a hetero atom between two carbon atoms, a group represented by —O—, a group represented by —NH—, or a group represented by —S—; $R^{3a}$ and $R^{3b}$ each independently represent a cyano group, a halogen atom, or a monovalent hydrocarbon group; and n1 and n2 each independently represent an integer of 0 to 4,

[Chem. 2]

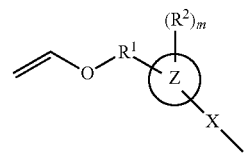

(2)

in which a ring Z represents an aromatic hydrocarbon ring; X represents a single bond or a group represented by —S—; $R^1$ represents a single bond or an alkylene group having 1 to 4 carbon atoms; $R^2$ represents a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a sulfo group, or a group formed by substituting at least a part of hydrogen atoms bonded to carbon atoms contained in a monovalent hydrocarbon group, a group represented by —$OR^{4a}$, a group represented by —$SR^{4b}$, an acyl group, an alkoxycarbonyl group, a group represented by —$NHR^{4c}$, or a group represented by —$N(R^{4d})_2$ with a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a mesyloxy group, or a sulfo group; $R^{4a}$ to $R^{4d}$ each independently represent a monovalent hydrocarbon group; and m is an integer of 0 or more, and

[Chem. 3]

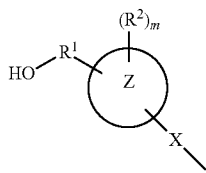
(4)

in which a ring Z, X, $R^1$, $R^2$, and m are as defined above.

According to a second aspect of the present invention, there is provided a method for producing a transparent body, in which the method includes heating a compound containing a monovinyl group and a mono(meth)acryloyloxy group at or above a melting point of the compound, and the compound is represented by the following general formula (10):

[Chem. 4]

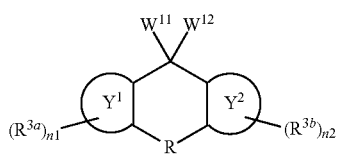
(10)

in which any one of $W^{11}$ and $W^{12}$ represents a group represented by the following general formula (2) while the other represents a group represented by the following general formula (11) or (12); and a ring $Y^1$, a ring $Y^2$, R, $R^{3a}$, $R^{3b}$, n1, and n2 are as defined above,

[Chem. 5]

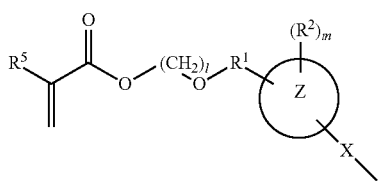
(11)

in which $R^5$ represents a hydrogen atom or a methyl group; l is an integer of 1 to 4; and a ring Z, X, $R^1$, $R^2$, and m are as defined above.

[Chem. 6]

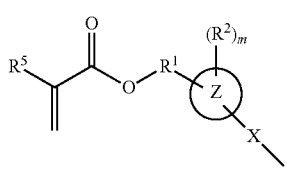
(12)

in which a ring Z, X, $R^1$, $R^2$, $R^5$, and m are as follows.

According to a third aspect of the present invention, there is provided a method for producing a transparent body, in which the method includes heating a compound containing a (meth)acryloyloxy group at or above a melting point of the compound, and the compound is represented by the following general formula (19):

[Chem. 7]

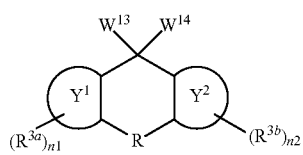
(19)

in which $W^{13}$ and $W^{14}$ each independently represent a group represented by the above general formula (12), a hydroxyl group, or a (meth)acryloyloxy group, provided that at least one of $W^{13}$ and $W^{14}$ represents a group represented by the above general formula (12); and a ring $Y^1$, a ring $Y^2$, R, $R^{3a}$, $R^{3b}$, n1, and n2 are as defined above.

According to a fourth aspect of the present invention, there is provided a transparent body obtained by the above production method.

According to a fifth aspect of the present invention, there is provided an amorphous body including a vinyl-group-containing compound represented by the following general formula (1).

Effects of the Invention

The present invention provides a transparent body production method using a novel vinyl-group-containing compound, and a transparent body obtained by the production method.

PREFERRED MODE FOR CARRYING OUT THE INVENTION

<<Method for Producing Transparent Body>>

Figure 1:
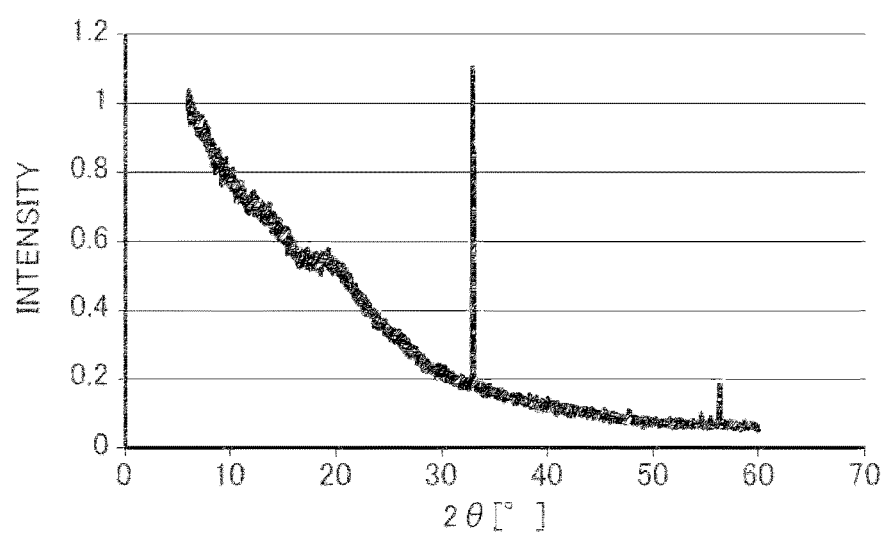
FIG. 1 is a graph illustrating an X-ray diffraction pattern of a transparent film 1 in Example 1 obtained by X-ray diffraction measurement.

The method for producing a transparent body according to the present invention includes heating a vinyl-group-containing compound represented by the above general formula (1), a compound containing a monovinyl group and a mono(meth)acryloyloxy group represented by the above general formula (10), and/or a compound containing a (meth)acryloyloxy group represented by the above general formula (19), at or above a melting point of the compound. The compound is melted by the heating. For example, a transparent body can be obtained by cooling the compound melted by the heating to a temperature at or below the melting point of the compound for solidification or by further heating the compound melted by the heating for curing. The melting point of the compound is a vale measured at one atm by differential calorimetric/thermogravimetric measurement.

The upper limit of the heating temperature is not particularly limited as long as a transparent body is obtained. Examples of the upper limit may include a temperature of (Tm+300)° C. or below, and preferably (Tm+200)° C. or below, in which Tm represents the melting point of the compound, ° C. When the upper limit of the heating temperature is in the above range, volatilization and decomposition of the melted compound can be suppressed. When the compound is cured by heating, examples of the curing temperature may include a temperature of 150 to 300° C.

Preferably, the heating is carried out in the absence of oxygen. The heating in the absence of oxygen is advantageous, for example, in that the compound is less likely to be oxidized, making it possible to suppress coloring of the transparent body. More specifically, the heating is preferably carried out in an inert atmosphere. Examples of such inert atmospheres may include a nitrogen atmosphere; and noble atmospheres such as an argon atmosphere. Inert atmospheres may be used solely or in a combination of two or more of them.

Preferably, the heating is carried out in such a state that the compound is not present together with a solvent. When the heating is carried out in such a state that the compound is not present together with a solvent, the influence of the solvent that stays in the resultant transparent body is likely to be suppressed.

In the method for producing a transparent body according to the present invention, a transparent body can be obtained as a transparent film by forming a film from a melt of the compound, and a transparent body can be obtained as a transparent molded product by molding a melt of the compound. The method for forming a film is not limited in particular; and examples thereof may include a method, in which the film is formed by coating a melt of the compound on a substrate such as a glass substrate or a silicon substrate and solidifying or curing the coating as described above. Examples of molding methods may include injection molding.

The above compounds will be described in more detail as follows.

<Vinyl-Group-Containing Compounds Represented by General Formula (1)>

Vinyl-group-containing compounds that may be contained in the composition according to the present invention are represented by the following general formula (1). The vinyl-group-containing compounds may be used solely or in a combination of two or more of them.

[Chem. 8]

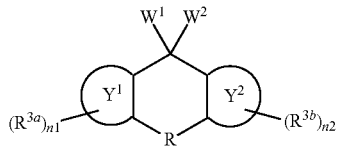
(1)

In the general formula (1), $W^1$ and $W^2$ each independently represent a group represented by the following general formula (2), a group represented by the following general formula (4), a hydroxyl group, or a (meth)acryloyloxy group, provided that $W^1$ and $W^2$ do not simultaneously represent a hydroxyl group or a group represented by the following general formula (4). Preferably, at least one of $W^1$ and $W^2$ represents a group represented by the following general formula (2). More preferably, both $W^1$ and $W^2$ are groups represented by the following general formula (2). Meanwhile, the term "(meth)acryloyl" as used in this specification means both acryloyl and methacryloyl.

[Chem. 9]

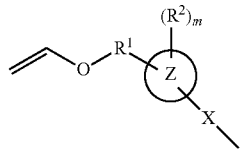
(2)

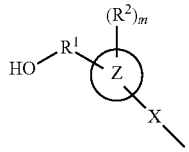
(4)

In the general formulae (2) and (4), examples of the ring Z may include benzene ring and fused polycyclic aromatic hydrocarbon rings [for example, fused di- to tetracyclic aromatic hydrocarbon rings such as fused dicyclic hydrocarbon rings (for example, $C_{8-20}$ fused dicyclic hydrocarbon rings, preferably $C_{10-16}$ fused dicyclic hydrocarbon rings, such as naphthalene ring) and fused tricyclic aromatic hydrocarbon rings (for example, anthracene ring or phenanthrene ring). The ring Z is preferably a benzene ring or a naphthalene ring, and more preferably a naphthalene ring. When both $W^1$ and $W^2$ represent a group represented by the general formula (2), or when one of $W^1$ and $W^2$ represent a group represented by the general formula (2) while the other represents a group represented by the general formula (4), the ring Z contained in $W^1$ may be the same as or different from the ring Z contained in $W^2$. For example, one of the rings may represent a benzene ring with the other ring representing a naphthalene ring or the like. Particularly preferably, both the rings represent a naphthalene ring. The position of substitution of the ring Z bonded through X to a carbon atom to which both $W^1$ and $W^2$ are directly bonded is not particularly limited. For example, when the ring Z represents a naphthalene ring, the group corresponding to the ring Z bonded to the carbon atom may be, for example, a 1-naphthyl group or a 2-naphthyl group.

In the general formulae (2) and (4), X each independently represent a single bond or a group represented by —S—, typically a single bond.

In the general formulae (2) and (4), examples of $R^1$ may include single bond; and alkylene groups having 1 to 4 carbon atoms such as methylene, ethylene, trimethylene, propylene, and butane-1,2-diyl groups. Single bond and $C_{2-4}$ alkylene groups (particularly $C_{2-3}$ alkylene groups such as ethylene and propylene groups) are preferred, and a single bond is more preferred. When both $W^1$ and $W^2$ represent a group represented by the general formula (2), or when one of $W^1$ and $W^2$ represents a group represented by the general formula (2) while the other represents a group represented by the general formula (4), $R^1$ contained in $W^1$ may be the same as or different from $R^1$ contained in $W^2$.

In the general formulae (2) and (4), examples of $R^2$ may include monovalent hydrocarbon group such as alkyl groups (for example, $C_{1-12}$ alkyl groups such as methyl, ethyl, propyl, isopropyl, and butyl groups, preferably $C_{1-8}$ alkyl groups, more preferably $C_{1-6}$ alkyl groups), cycloalkyl groups (for example, $C_{5-10}$ cycloalkyl groups such as cyclohexyl group, preferably $C_{5-8}$ cycloalkyl groups, more preferably $C_{5-6}$ cycloalkyl groups), aryl groups (for example, $C_{6-14}$ aryl groups such as phenyl, tolyl, xylyl, and naphthyl groups, preferably $C_{6-10}$ aryl groups, more preferably $C_{6-8}$ aryl groups), and aralkyl groups (for example, $C_{6-10}$ aryl $C_{1-4}$ alkyl groups such as benzyl and phenethyl groups); hydroxyl group; groups represented by $—OR^{4a}$ in which $R^{4a}$ represents a monovalent hydrocarbon group (for example, the above-exemplified monovalent hydrocarbon group) such as alkoxy groups (for example, $C_{1-12}$ alkoxy groups such as methoxy, ethoxy, propoxy, and butoxy groups, preferably $C_{1-8}$ alkoxy groups, more preferably $C_{1-6}$ alkoxy groups), cycloalkoxy groups ($C_{5-10}$ cycloalkoxy groups such as cyclohexyloxy groups), aryloxy groups ($C_{6-10}$ aryloxy groups such as phenoxy group), and aralkyloxy groups (for example, $C_{6-10}$ aryl $C_{1-4}$ alkyloxy groups such as benzyloxy group);

groups represented by $—SR^{4b}$ in which $R^{4b}$ represents a monovalent hydrocarbon group (for example, the above-exemplified monovalent hydrocarbon group) such as alkylthio groups (for example, $C_{1-12}$ alkylthio groups such as methylthio, ethylthio, propylthio, and butylthio groups, preferably $C_{1-8}$ alkylthio groups, more preferably $C_{1-6}$ alkylthio groups), cycloalkylthio groups (for example, $C_{5-10}$ cycloalkylthio groups such as cyclohexylthio groups), aryl thio groups ($C_{6-10}$ aryl thio groups such as phenylthio), and aralkyl thio groups (for example, $C_{6-10}$ aryl $C_{1-4}$ alkylthio groups such as benzylthio groups);

acyl groups ($C_{1-6}$ acyl groups such as acetyl group); alkoxycarbonyl groups (for example, $C_{1-4}$ alkoxycarbonyl groups such as methoxycarbonyl group); halogen atoms (for example, a fluorine atom, a chlorine atom, a bromine atom, and an iodine atom); nitro group; cyano group; mercapto group; carboxyl group; amino group; carbamoyl group; groups represented by $—NHR^{4c}$ in which $R^{4c}$ represents a monovalent hydrocarbon group (for example, the above-exemplified monovalent hydrocarbon group) such as alkylamino groups ($C_{1-12}$ alkylamino groups such as methylamino group, ethylamino group, propylamino group, and butylamino group, preferably $C_{1-8}$ alkylamino groups, more preferably $C_{1-6}$ alkylamino groups), cycloalkylamino groups (for example, $C_{5-10}$ cycloalkylamino groups such as cyclohexylamino group), arylamino groups ($C_{6-10}$ aryl amino groups such as phenylamino group), and aralkyl amino groups (for example, $C_{6-10}$ aryl $C_{1-4}$ alkylamino groups such as benzylamino group) groups represented by $—N(R^{4d})^2$ in which $R^{4d}$ each independently represents a monovalent hydrocarbon group (for example, the above-exemplified monovalent hydrocarbon group) such as dialkylamino groups (di($C_{1-12}$ alkyl)amino groups such as dimethylamino group, diethylamino group, dipropylamino group, and dibutylamino group, preferably di($C_{1-8}$ alkyl)amino groups, more preferably di($C_{1-6}$ alkyl)amino groups), dicycloalkylamino groups (di($C_{5-10}$cycloalkyl)amino groups such as dicyclohexylamino group), diaryl amino groups (di($C_{6-10}$ aryl)amino groups such as diphenylamino group), and diaralkyl amino groups (for example, di($C_{6-10}$ aryl $C_{1-4}$ alkyl) amino groups such as dibenzylamino group);

(meth)acryloyloxy groups; sulfo group; and the above monovalent hydrocarbon groups, groups represented by $—OR^{4a}$, groups represented by $—SR^{4b}$, acyl groups, alkoxycarbonyl groups, groups represented by $—NHR^{4c}$, or groups formed by substituting at least a part of hydrogen atoms bonded to carbon atoms contained in groups represented by $—N(R^{4d})^2$ with the above monovalent hydrocarbon group, a hydroxyl group, a group represented by $—OR^{4a}$, a group represented by $—SR^{4b}$, an acyl group, an alkoxycarbonyl group, a halogen atom, a nitro group, a cyano group, a mercapto group, a carboxyl group, an amino group, a carbamoyl group, a group represented by $—NHR^{4c}$, a group represented by $—N(R^{4d})_2$, a (meth)acryloyloxy group, a mesyloxy group, or a sulfo group [for example, alkoxyaryl groups (for example, $C_{1-4}$ alkoxy $C_{6-10}$ aryl groups such as methoxyphenyl group), alkoxycarbonylaryl groups (for example, $C_{1-4}$ alkoxycarbonyl $C_{6-10}$ aryl groups such as methoxycarbonylphenyl group and ethoxycarbonylphenyl)].

Among them, typical examples of $R^2$ include monovalent hydrocarbon groups, groups represented by $—OR^{4a}$, groups represented by $—SR^{4b}$, acyl groups, alkoxycarbonyl groups, halogen atoms, nitro group, cyano group, groups represented by $—NHR^{4c}$, and groups represented by $—N(R^{4d})_2$.

Examples of preferred $R^2$ may include monovalent hydrocarbon groups [for example, alkyl groups (for example, $C_{1-6}$ alkyl groups), cycloalkyl groups (for example, $C_{5-8}$ cycloalkyl groups), aryl groups (for example, $C_{6-10}$ aryl groups), and aralkyl groups (for example, $C_{6-8}$ aryl $C_{1-2}$ alkyl groups)], and alkoxy groups (for example, $C_{1-4}$ alkoxy groups). In particular, preferably, $R^{2a}$ and $R^{2b}$ represent a monovalent hydrocarbon group such as an alkyl group [for example, a $C_{1-4}$ alkyl group (particularly a methyl group)], an aryl group [for example, a $C_{6-10}$ aryl group (particularly a phenyl group)] (particularly an alkyl group).

When m is an integer of 2 or more, $R^2$'s may be different from or the same as each other. When both $W^1$ and $W^2$ represent a group represented by the general formula (2), or when one of $W^1$ and $W^2$ represents a group represented by the general formula (2) while the other represents a group represented by the general formula (4), $R^2$ contained in $W^1$ may be the same as or different from $R^2$ contained in $W^2$.

In the general formulae (2) and (4), the number of $R^2$'s, that is, m, may be selected according to the type of the ring Z and may be, for example, 0 to 4, preferably 0 to 3, and more preferably 0 to 2. When both $W^1$ and $W^2$ represent a group represented by the general formula (2), or when one of $W^1$ and $W^2$ represents a group represented by the general formula (2) while the other represents a group represented by the general formula (4), $R^2$ contained in $W^1$ may be the same as or different from $R^2$ contained in $W^2$.

In the general formula (1), examples of the ring $Y^1$ and the ring $Y^2$ may include benzene ring and fused polycyclic aromatic hydrocarbon rings [for example, fused di- to tetracyclic aromatic hydrocarbon rings such as fused dicyclic hydrocarbon rings (for example, $C_{8-20}$ fused dicyclic hydrocarbon rings, preferably $C_{10-16}$ fused dicyclic hydrocarbon rings, such as naphthalene ring) and fused tricyclic aromatic hydrocarbon rings (for example, anthracene ring or phenanthrene ring)]. Preferably, the ring $Y^1$ and the ring $Y^2$ represent a benzene ring or a naphthalene ring. The ring $Y^1$ and the ring $Y^2$ may be the same or different. For example, one of the rings represents a benzene ring with the other ring representing a naphthalene ring.

In the general formula (1), R represents a single bond, an optionally substituted methylene group, an ethylene group that is optionally substituted and may contain a hetero atom between two carbon atoms, a group represented by $—O—$, a group represented by $—NH—$, or a group represented by $—S—$, typically represents a single bond. Examples of substituents may include a cyano group, halogen atoms (for example, a fluorine atom, a chlorine atom, a bromine atom, and an iodine atom), monovalent hydrocarbon groups [for example, alkyl groups ($C_{1-6}$alkyl groups such as methyl, ethyl, propyl, isopropyl, butyl, and t-butyl), and aryl groups ($C_{6-10}$ aryl groups such as a phenyl group). Examples of hetero atoms may include oxygen, nitrogen, sulfur, silicon atoms, etc.

In the general formula (1), general examples of $R^{3a}$ and $R^{3b}$ may include nonreactive substituents, for example, cyano group, halogen atoms (for example, fluorine atom, chlorine atom, and bromine atom), monovalent hydrocarbon groups [for example, alkyl groups and aryl groups ($C_{6-10}$ aryl groups such as phenyl group]. A cyano group or an alkyl group is preferred, and an alkyl group is particularly preferred. Examples of alkyl groups include $C_{1-6}$ alkyl groups (for example, $C_{1-4}$ alkyl groups, particularly methyl group) such as methyl, ethyl, propyl, isopropyl, butyl, and t-butyl groups. When n1 is an integer of 2 or more, $R^1$'s may be the same as or different from each other. When n2 is an integer of 2 or more, $R^{3b}$'s may be the same as or different from each other. Further, $R^{3a}$ and $R^{3b}$ may be the same as or different from each other. The position of bonding of $R^{3a}$ and $R^{3b}$ to the ring $Y^1$ and the ring $Y^2$ (position of substitution) is not particularly limited. The number of substituents n1 and n2 is preferably 0 (zero) or 1, and particularly preferably 0 (zero). n1 and n2 may be the same as or different from each other.

Compounds represented by the general formula (1) holds excellent optical properties and thermal properties and, at the same time, have a high reactivity by virtue of the presence of a vinyloxy group and/or a (meth)acryloyloxy group. In particular, when the ring $Y^1$ and the ring $Y^2$ represent a benzene ring while R represents a single bond, compounds represented by the general formula (1) have a fluorene skeleton and possess further improved optical properties and thermal properties. The compounds represented by the general formula (1) can be polymerized and thus function as polymerizable monomers. In particular, when both $W^1$ and $W^2$ represent a group represented by the general formula (2), the compounds represented by the general formula (1) can be cationically polymerized and thus can function as cationically polymerizable monomers. On the other hand, when both $W^1$ and $W^2$ represent a (meth)acryloyloxy group, the compounds represented by the general formula (1) can be radically polymerized and thus function as radically polymerizable monomers. In the compounds represented by the general formula (1) in which $W^1$ and $W^2$ each independently represent a group represented by the general formula (2) or a (meth)acryloyloxy group, two vinyl groups contained in the form of the vinyloxy group and/or the (meth)acryloyloxy group can be reacted with different molecules and, thus, the compounds represented by the general formula (1) are suitable as crosslinking agents. Further, the compounds represented by the general formula (1) can provide cured products having a high hardness and are preferred as a base component in the composition. In addition, when compounds represented by the general formula (1) are contained in negative-type photosensitive resin compositions, good micropatterning properties can be obtained. Compounds represented by the general formula (1) can be used in various applications, for example, alignment films and flattening films (for example, alignment films and flattening films used, for example, in liquid crystal displays and organic EL displays); resist underlying films such as antireflection films, interlayer insulating films, and carbon hard masks; spacers and partition walls such as liquid crystal displays and organic EL displays; pixels and black matrixes in color filters of liquid crystal displays; display devices such as liquid crystal displays and organic EL displays; lenses (for example, microlenses), optical members such as optical fibers, light waveguides, prism sheets, holograms, high refractive index films, and retroreflection films; low moisture permeable membranes (for example, low moisture permeable membranes used as water vapor barrier layers; optical materials; and semiconductor materials.

As described above, when the ring $Y^1$ and the ring $Y^2$ represent a benzene ring while R represents a single bond, compounds represented by the general formula (1) are preferred because the compounds have a fluorene skeleton and possess further improved properties in terms of optical properties such as optical transmittance and refractive index and thermal properties. Further, in compounds represented by the general formula (1) in which both $W^1$ and $W^2$ represent a group represented by the general formula (2), X represents a single bond, and $R^1$ represents a single bond, further improved properties in terms of optical properties such as optical transmittance and refractive index are likely to be obtained. In particular, when $R^1$ represents a single bond, a significant improvement in optical properties and thermal properties is likely to be advantageously attained.

Among the compounds represented by the general formula (1), specific examples of particularly preferred compounds may include compounds represented by the following formulae.

[Chem. 10]

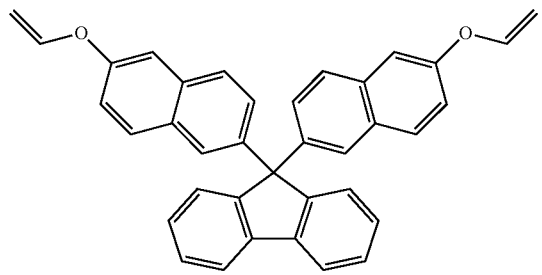

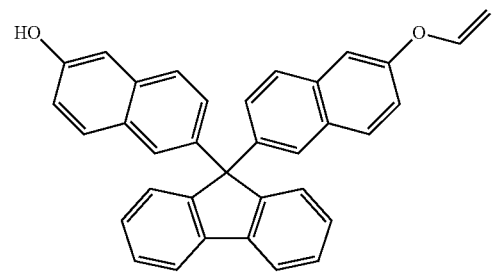

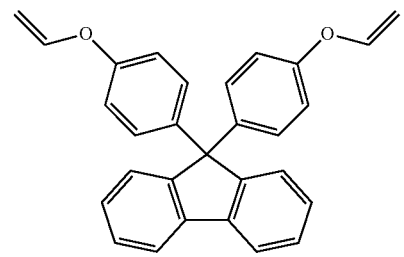

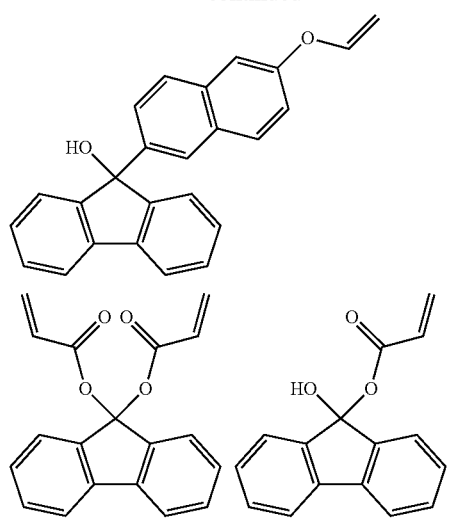
[Chem. 11]
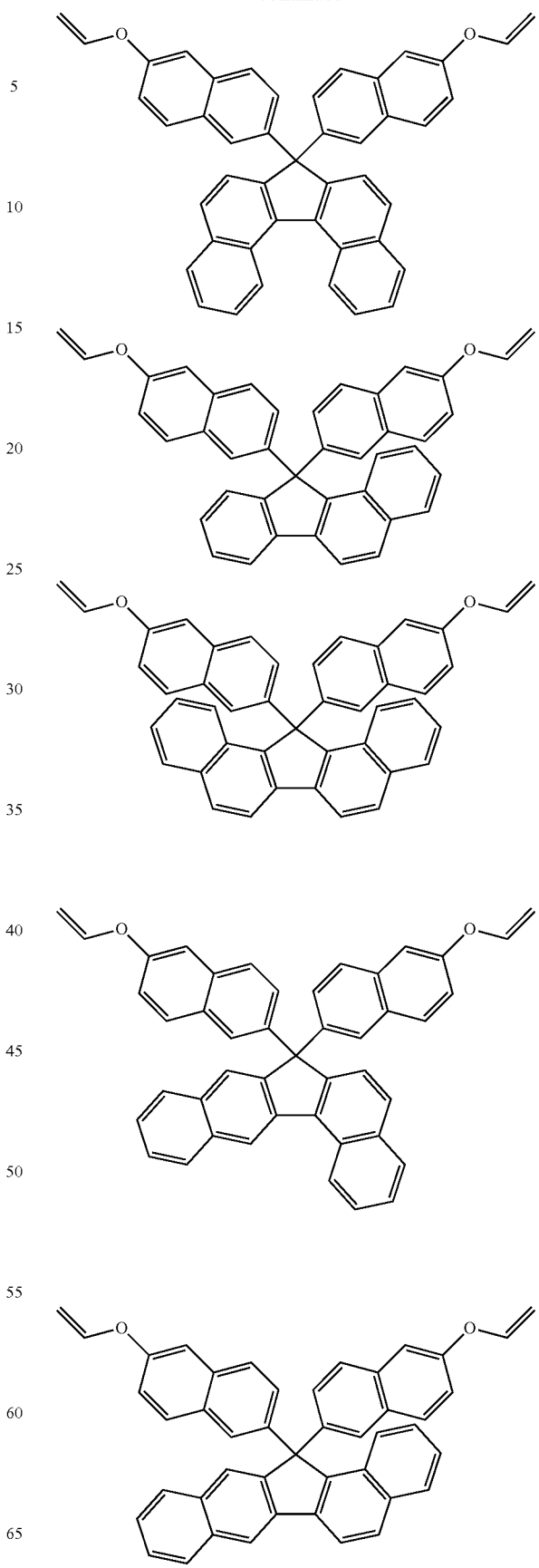

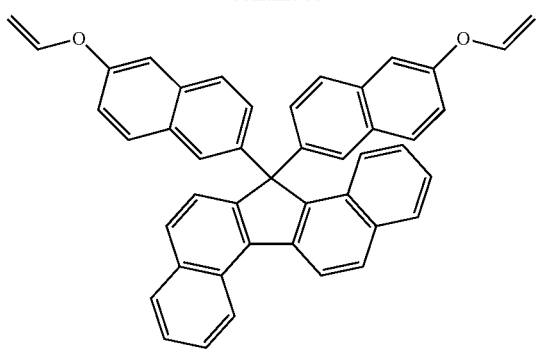
[Chem. 12]
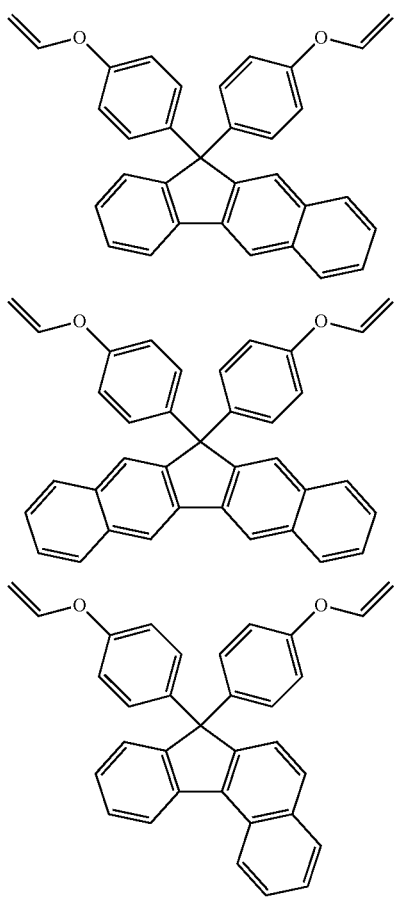
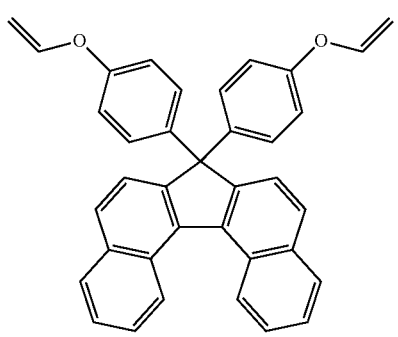
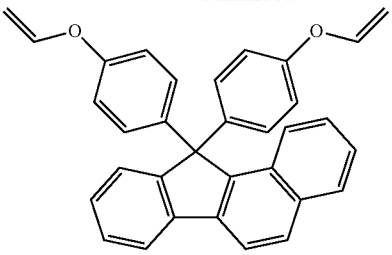
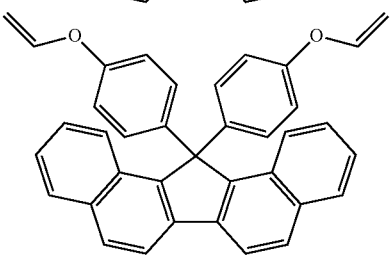
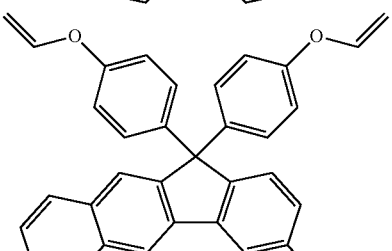
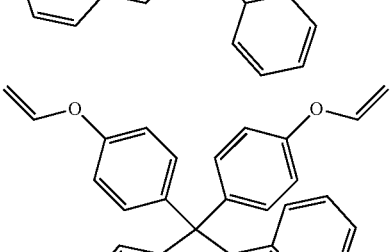
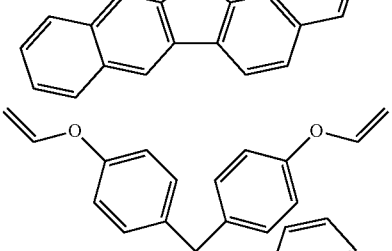
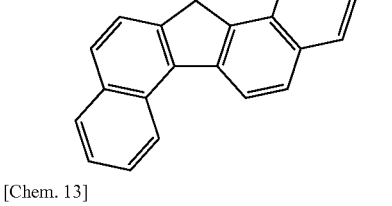
[Chem. 13]
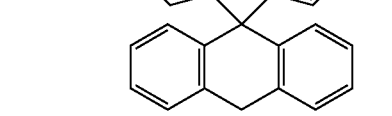

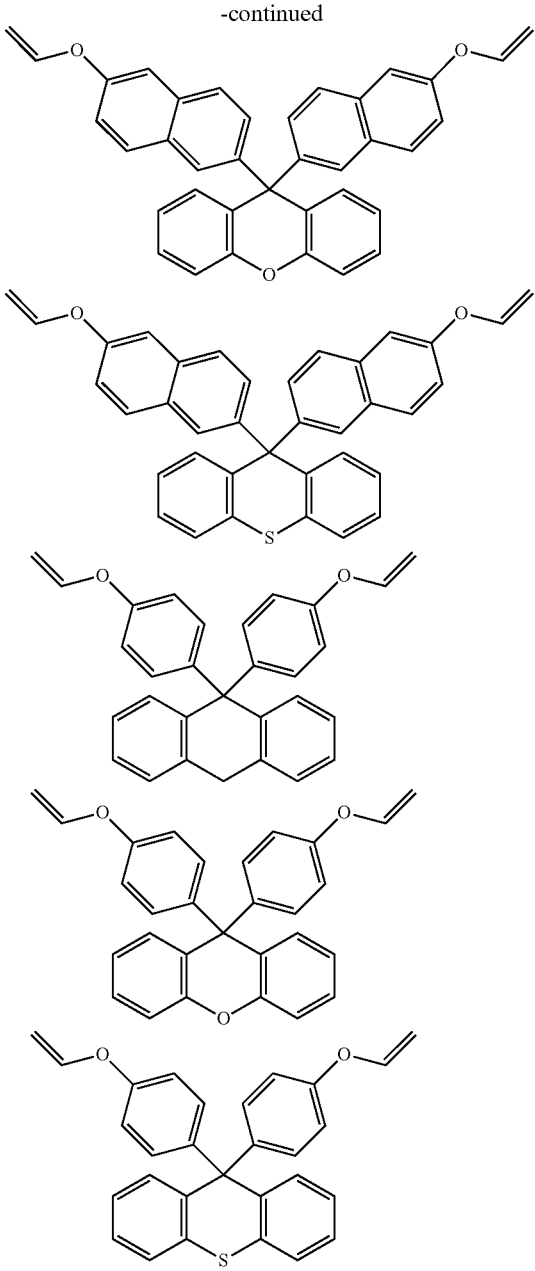

[Method for Producing Vinyl-Group-Containing Compounds Represented by General Formula (1a)]

Among the vinyl-group-containing compounds represented by the general formula (1), compounds represented by the general formula (1a) can be produced, for example, by the following production methods 1 to 3.

[Chem. 14]

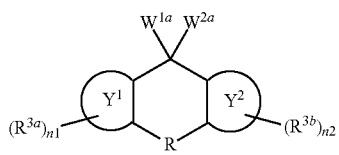

(1a)

in which $W^{1a}$ and $W^{2a}$ each independently represent a group represented by the general formula (2), a group represented by the general formula (4), a hydroxyl group, or a (meth)acryloyloxy group, provided that $W^{1a}$ and $W^{2a}$ do not simultaneously represent a hydroxyl group, a group represented by the general formula (4), or a (meth)acryloyloxy group; and the ring $Y^1$, the ring $Y^2$, R, $R^{3a}$, $R^{3b}$, n1, and n2 are as follows.

Production Method 1

Vinyl-group-containing compounds represented by the general formula (1a) can be synthesized, for example, according to a production method described in JP2008-266169A by reacting a vinyl ester compound represented by the general formula (13) with a hydroxyl group-containing compound represented by the general formula (3) in the presence of a transition element compound catalyst and an inorganic base. The inorganic base is preferably a solid inorganic base containing not less than 10% by weight of particles having a diameter of less than 150 μm. Specifically, vinyl-group-containing compounds represented by the general formula (1a) can be synthesized as described in Synthesis Examples 1 to 3 that will be described later.

$$R^6-CO-O-CH=CH_2 \qquad (13)$$

in which $R^6$ represents a hydrogen atom or an organic group.

[Chem. 15]

(3)

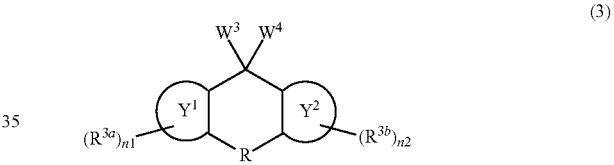

in which $W^3$ and $W^4$ each independently represent a group represented by the following general formula (4) or a hydroxyl group, provided that $W^3$ and $W^4$ do not simultaneously represent a hydroxyl group; and the ring $Y^1$, the ring $Y^2$, R, $R^{3a}$, $R^{3b}$, n1, and n2 are as defined above.

[Chem. 16]

(4)

in which the ring Z, X, $R^1$, $R^2$, and m are as defined above.

Compounds represented by the general formula (3) can be synthesized, for example, by reacting a compound represented by the following general formula (14) and/or a compound represented by the following general formula (15) with a compound represented by the general formula (16) in the presence of an acid catalyst. Desired hydroxyl group-containing compounds represented by the general formula (3) can be obtained by properly regulating a combination of compounds represented by the general formula (14) and compounds represented by the general formula (15) and the addition amounts of the compounds. After the reaction, contemplated hydroxyl group-containing compounds may be separated by publicly known separation methods, for example, silica gel column chromatography.

[Chem. 17]

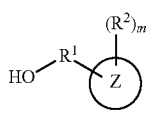

(14)

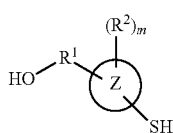

(15)

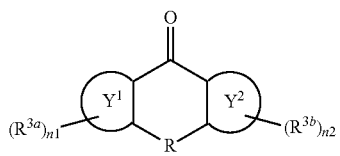

(16)

In the general formulae (14), (15), and (16), the ring $Y^1$, the ring $Y^2$, the ring Z, R, $R^1$, $R^2$, $R^{3a}$, $R^{3b}$, m, n1, and n2 are as defined above.

Examples of acid catalysts usable in the synthesis of compounds represented by the general formula (3), reaction condition and the like may include those disclosed in Patent Document 1 or JP2002-255929A to the effect that are used in the production method of fluorene-based compounds disclosed in the claims thereof.

Production Method 2

Compounds represented by the general formula (1a) can also be synthesized by a production method that includes obtaining vinyl-group-containing compounds represented by the general formula (1a) from hydroxyl group-containing compounds represented by the general formula (3) through leaving group-containing compounds represented by the general formula (5).

[Chem. 18]

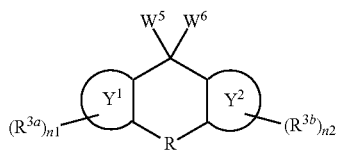

(5)

in which $W^5$ and $W^6$ each independently represent a group represented by the general formula (6) or a hydroxyl group, provided that $W^5$ and $W^6$ do not simultaneously represent a hydroxyl group; and the ring $Y^1$, the ring $Y^2$, R, $R^{3a}$, $R^{3b}$, n1, and n2 are as follows.

[Chem. 19]

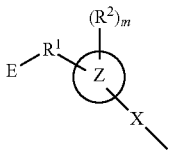

(6)

in which E represents an alkyloxy group having 1 to 4 carbon atoms substituted by a chlorine atom, a bromine atom, an iodine atom, a methanesulfonyloxy group, a trifluoromethanesulfonyloxy group, a p-toluenesulfonyloxy group, or a benzenesulfonyloxy group; and a ring Z, X, $R^1$, $R^2$, and m are as defined above.

Leaving group-containing compounds represented by the general formula (5) can be synthesized, for example, by reacting hydroxyl group-containing compounds represented by the general formula (3) with leaving group-containing compounds. Examples of leaving group-containing compounds may include thionyl chloride, compounds represented by the following formula, etc. Examples of the reaction temperature may include a temperature of −20 to 150° C., preferably −10 to 140° C., and more preferably 30 to 130° C.

[Chem. 20]

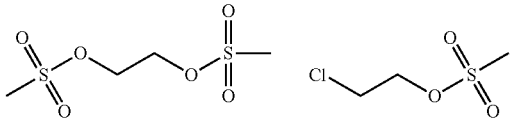

Vinyl-group-containing compounds represented by the general formula (1a) can be synthesized, for example, by reacting leaving group-containing compounds represented by the general formula (5) with vinylating agents. Examples of vinylating agents may include sodium hydroxide, triethylamine, diisopropyl ethylamine, 1,4-diazabicyclo[2.2.2]octane, diazabicyclo undecene, sodium methoxide, sodium ethoxide, sodium ethoxide, and potassium t-butoxide. Preferred are diazabicyclo undecene, sodium ethoxide, potassium t-butoxide, etc., among which potassium t-butoxide may be more preferable. Examples of the reaction temperature may include a temperature of −20 to 150° C., preferably −10 to 100° C., and more preferably 0 to 60° C.

Production Method 3

Compounds represented by the general formula (1a) can also be synthesized, for example, by a production method that includes obtaining vinyl-group-containing compounds represented by the general formula (1a) from hydroxyalkyloxy group-containing compounds represented by the general formula (7) through leaving group-containing compounds represented by the general formula (5). Specifically, compounds represented by the general formula (1a) can be synthesized as described in Synthesis Examples 4 and 5 and Synthesis Examples 12 and 13.

[Chem. 21]

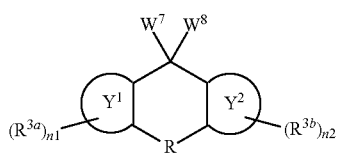

(7)

in which $W^7$ and $W^8$ each independently represent a group represented by the general formula (8) or a hydroxyl group, provided that $W^7$ and $W^8$ do not simultaneously represent a hydroxyl group; and a ring $Y^1$, a ring $Y^2$, R, $R^{3a}$, $R^{3b}$, n1, and n2 are as defined above.

[Chem. 22]

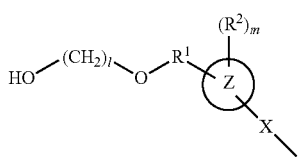

(8)

in which l is an integer of 1 to 4; a ring Z, X, $R^1$, $R^2$, and m are as defined above.

Hydroxyalkyloxy group-containing compounds represented by the above general formula (7) can be synthesized, for example, by reacting compounds represented by the following general formula (17) and/or compounds represented by the following general formula (18) with compounds represented by the general formula (16) in the presence of an acid catalyst. Desired hydroxyalkyloxy group-containing compounds represented by the above general formula (7) can be obtained by properly regulating a combination of compounds represented by the following general formula (17) and compounds represented by the following general formula (18) and the addition amounts of the compounds. After the reaction, contemplated hydroxyalkyloxy group-containing compounds may be separated, for example, by publicly known separation methods such as silica gel column chromatography. Examples of acid catalysts, reaction conditions and the like usable in the synthesis of compounds represented by the general formula (7) may include those exemplified in the description of the synthesis method of compounds represented by the general formula (3).

[Chem. 23]

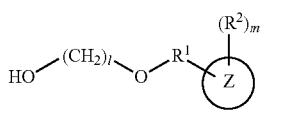

(17)

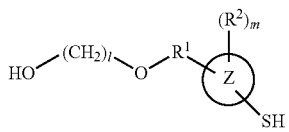

(18)

in which, in the general formulae (17) and (18), a ring Z, $R^1$, $R^2$, and m are as defined above.

Leaving group-containing compounds represented by the above general formula (5) can be synthesized, for example, by reacting hydroxyalkyloxy group-containing compounds represented by the above general formula (7) with leaving group-containing compounds. Examples of the leaving group-containing compound and the reaction temperature may include those exemplified in the description of the production method 2.

Vinyl-group-containing compounds represented by the above general formula (1a) can be synthesized, for example, by reacting leaving group-containing compounds represented by the general formula (5) with vinylating agents. Examples of the vinylating agent and the reaction temperature may include those exemplified in the production method 2.

According to the production method 3, compounds represented by the general formula (1a) can be obtained from hydroxyalkyloxy group-containing compounds represented by the general formula (7) at a high yield. For example, the yield of 9,9'-bis(6-vinyloxy-2-naphthyl)fluorene was 77% in Synthesis Examples 4 and 5, and the yield of 9,9'-bis(4-vinyloxyphenyl)fluorene was 79% in Synthesis Examples 12 and 13. According to the production method 3, the load in the step of purification of compounds represented by the general formula (1a) can be reduced. Further, in the production method 3, the reaction can be carried out at ordinary pressures, and, thus, special reaction facilities such as heat-resistant vessels are unnecessary, making it possible to use simpler apparatuses. Further, in the production method 3, flammable gases such as acetylene gas are not used, and, thus, compounds represented by the general formula (1a) can be produced more safely.

<Purification Method>

Vinyl-group-containing compounds represented by the general formula (1) may be purified after the synthesis. The purification method is not limited in particular; and examples thereof may include publicly known methods such as silica gel column chromatography. The purification can result in an improvement in purity of vinyl-group-containing compounds represented by the general formula (1) and a reduction in content of the metallic component. The use of purified vinyl-group-containing compounds is likely to contribute to an improvement in reactivity and, at the same time, can contribute to effective suppression of coloring during the reaction.

Leaving Group-Containing Compounds Represented by General Formula (5)

Leaving group-containing compounds represented by the above general formula (5) are useful as intermediate compounds for the production of vinyl-group-containing compounds represented by the general formula (1a). Leaving group-containing compounds represented by the above general formula (5) can be synthesized, for example, by the methods described above in connection with the production method 2 or 3.

Monovinyl-Group-Containing Compounds Represented by the General Formula (9) and a Method for Production Thereof Monovinyl-group-containing compounds represented by the following general formula (9) are useful as intermediate compounds for the production of vinyl-group-containing compounds represented by the above general formula (1a).

[Chem. 24]

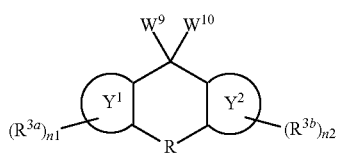

(9)

in which any one of $W^9$ and $W^{10}$ represents a group represented by the general formula (2) while the other represents a group represented by the general formula (6); and a ring $Y^1$, a ring $Y^2$, R, $R^{3a}$, $R^{3b}$, n1, and n2 are as defined above.

Monovinyl-group-containing compounds represented by the general formula (9) can be synthesized by a production method that includes monovinyl-group-containing compounds represented by the general formula (9) from leaving group-containing compounds represented by the general formula (5a). Specifically, monovinyl-group-containing compounds represented by the general formula (9) can be synthesized as described in Synthesis Examples 8 and 11 that will be described later. That is, monovinyl-group-containing compounds represented by the general formula (9) can be synthesized, for example, by reacting leaving group-containing compounds represented by the above general formula (5a) with vinylating agents. Examples of the vinylating agent and the reaction temperature may include those exemplified in the production method 2. The amount of the vinylating agent used is preferably 0.1 to 10 moles, more preferably 0.5 to 5 moles, and still more preferably 0.8 to 2 moles, per mole of the leaving group in the leaving group-containing compound represented by the above general formula (5a).

[Chem. 25]

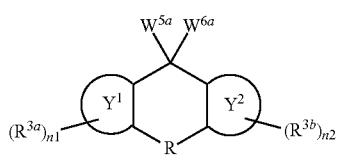

(5a)

in which $W^{5a}$ and $W^{6a}$ represent a group represented by the general formula (6); and a ring $Y^1$, a ring $Y^2$, $R^{3a}$, $R^{3b}$, n1, and n2 are as defined above.

<Monovinyl-Group- and Mono(Meth)Acryloyloxy-Group-Containing Compounds Represented by the General Formula (10)>

Monovinyl-group- and mono(meth)acryloyloxy-group-containing compounds contained in the compound according to the present invention are represented by the following general formula (10). The monovinyl-group- and mono (meth)acryloyloxy-group-containing compounds may be used either solely or in combination of two or more of them. The compounds have a high reactivity by virtue of the presence of the vinyloxy group and the (meth)acryloyloxy group while maintaining excellent optical properties and thermal properties characteristic of compounds containing a hydroxyl group and a (meth)acryloyloxy group. In particular, when a ring $Y^1$ and a ring $Y^2$ represent a benzene ring and R represents a single bond, compounds represented by the following general formula (10) have a fluorene skeleton and possess further improved optical properties and thermal properties. As with vinyl-group-containing compounds represented by the general formula (1), compounds represented by the following general formula (10) can be polymerized and thus function as polymerizable monomers and are suitable as crosslinking agents. Further, compounds represented by the general formula (10) can provide cured products having a high hardness and thus are preferred as a base component in the composition. In addition, when compounds represented by the general formula (10) are incorporated in negative-type photosensitive resin compositions, good micropatterning properties can be obtained. Compounds represented by the following general formula (10) can be used in various applications, for example, in applications that have been specifically exemplified in connection with the compounds represented by the general formula (1).

[Chem. 26]

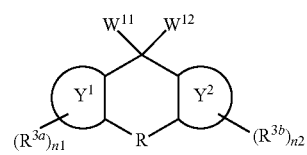

(10)

in which any one of $W^{11}$ and $W^{12}$ represents a group represented by the following general formula (2) while the other represents a group represented by the following general formula (11) or (12); and a ring $Y^1$, a ring $Y^2$, R, $R^{3a}$, $R^{3b}$, n1, and n2 are as defined above.

[Chem. 27]

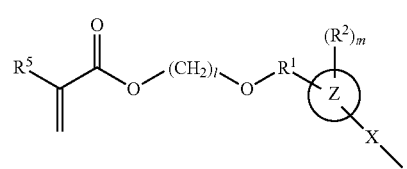

(11)

in which $R^5$ represents a hydrogen atom or a methyl group; and a ring Z, X, $R^1$, $R^2$, m, and l are as defined above, and

[Chem. 28]

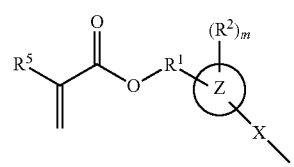

(12)

in which a ring Z, X, $R^1$, $R^2$, $R^5$, and m are as defined above.

<(Meth)Acryloyloxy-Group-Containing Compounds Represented by General Formula (19)>

(Meth)acryloyloxy-group-containing compounds contained in the composition according to the present invention are represented by the following general formula (19). The (meth)acryloyloxy-group-containing compounds may be used either solely or in a combination of two or more of them. The compounds have a high reactivity by virtue of the presence of the vinyloxy group and the (meth)acryloyloxy group while maintaining excellent optical properties and thermal properties. In particular, when a ring $Y^1$ and a ring $Y^2$ represent a benzene ring and R represents a single bond, compounds represented by the following general formula (19) have a fluorene skeleton and possess further improved optical properties and thermal properties. As with vinyl-group-containing compounds represented by the general formula (1), compounds represented by the following general formula (19) can be polymerized and thus function as polymerizable monomers and are suitable as crosslinking agents. Further, compounds represented by the general formula (19) can provide cured products having a high hardness and thus are preferred as a base component in the composition. In addition, when compounds represented by the general formula (19) are incorporated in negative-type photosensitive resin compositions, good micropatterning properties can be obtained. Compounds represented by the above general formula (19) can be used in various applications, for example, in applications that have been specifically exemplified in connection with the compounds represented by the general formula (1).

[Chem. 29]

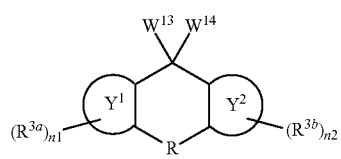

(19)

in which $W^{13}$ and $W^{14}$ each independently represent a group represented by the general formula (12), a hydroxyl group, or a (meth)acryloyloxy group, provided that at least one of $W^{13}$ and $W^{14}$ represents a group represented by the general formula (12); and a ring $Y^1$, a ring $Y^2$, R, $R^{3a}$, $R^{3b}$, n1, and n2 are as defined above.

Among the compounds represented by the general formula (19), specific examples of particularly preferred compounds may include compounds represented by the following formulae.

[Chem. 30]

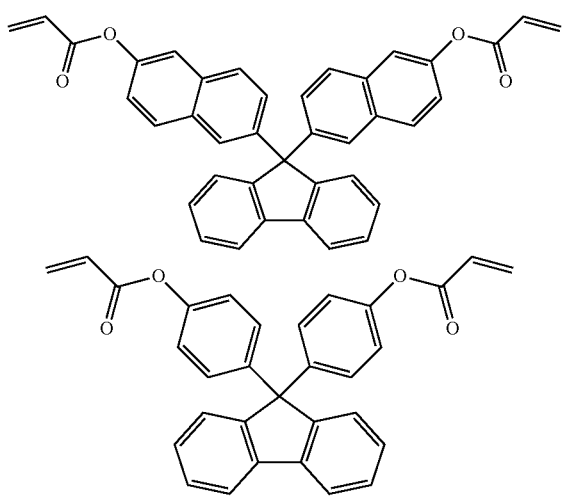

[Chem. 31]

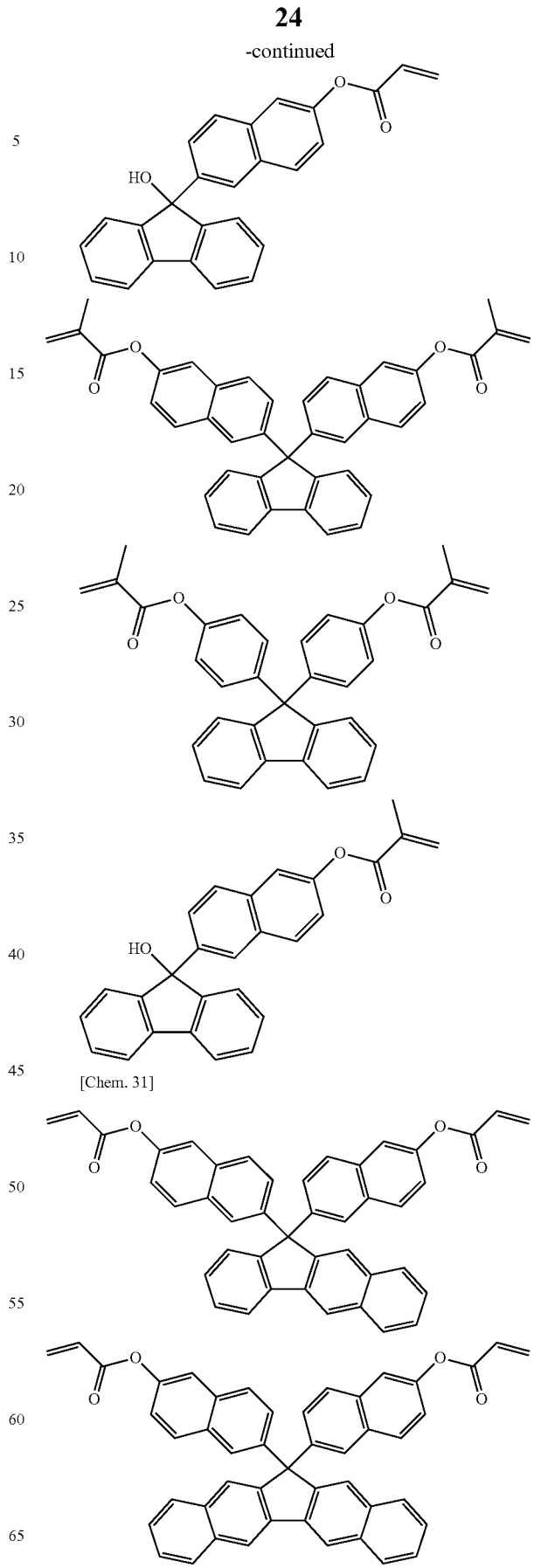

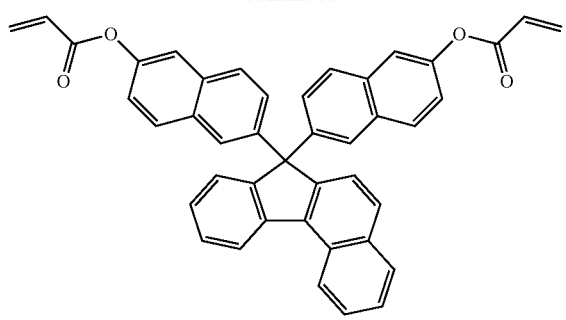
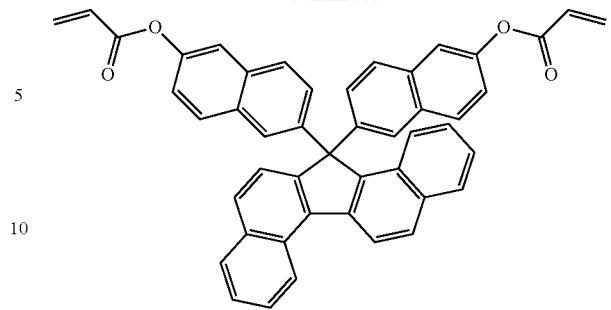
[Chem. 32]
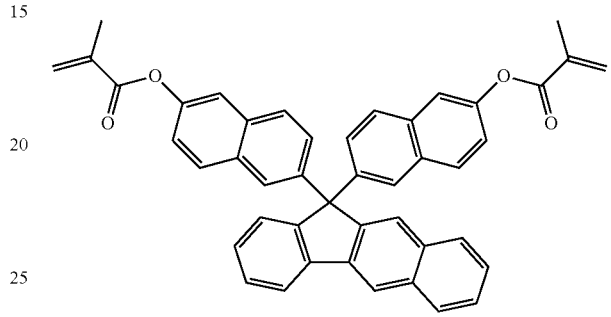
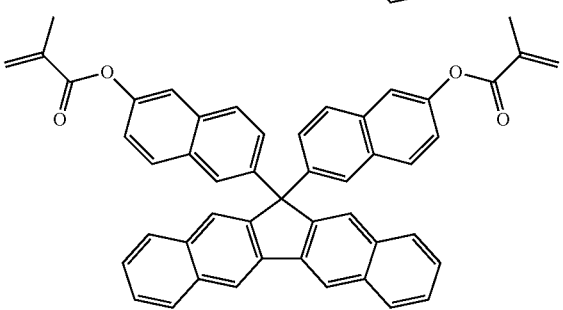
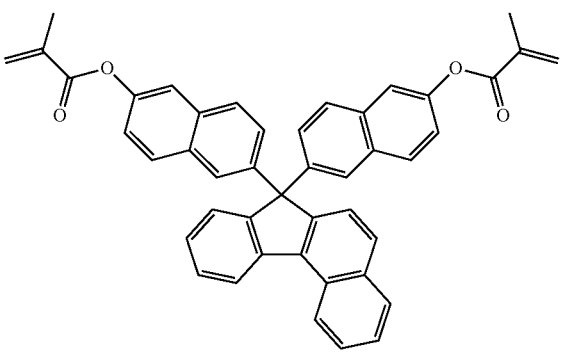
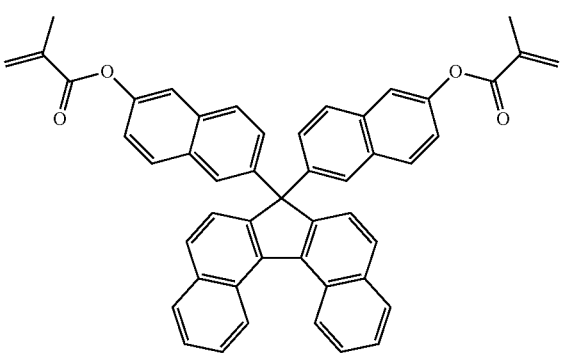

-continued

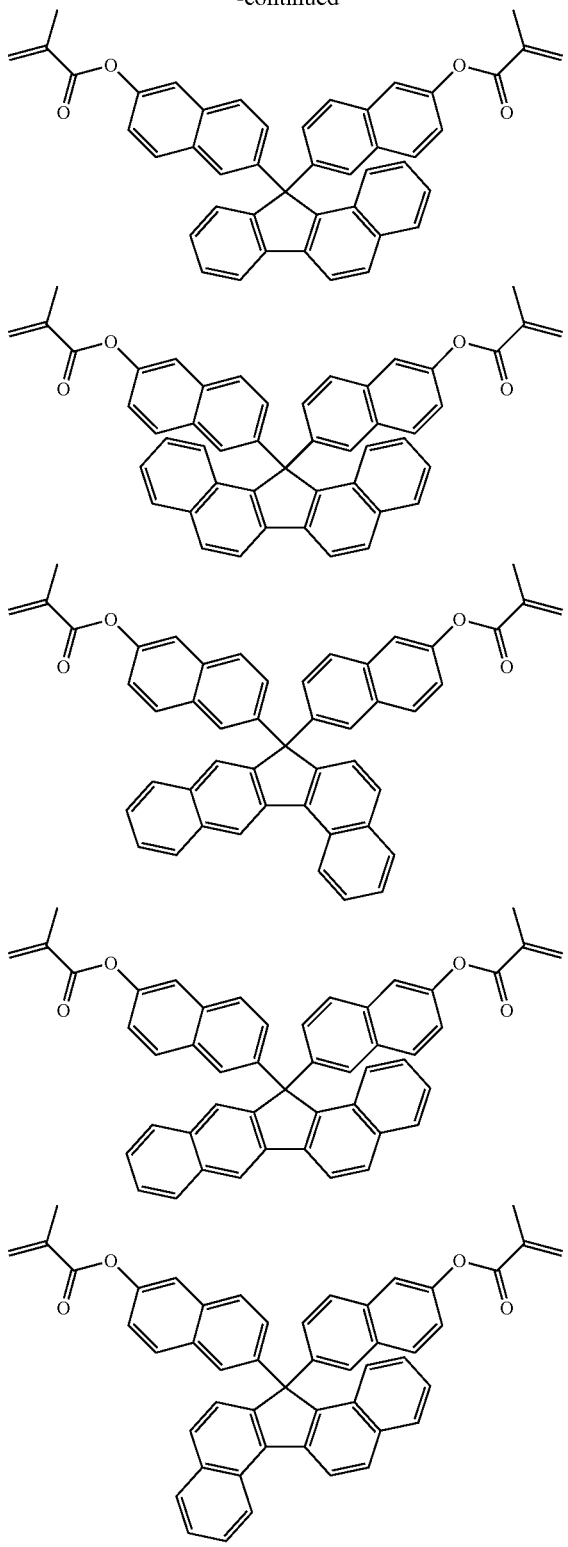

[Production Method of (Meth)Acryloyloxy Group-Containing Compounds Represented by General Formula (19)]

Compounds represented by the general formula (19) can also be synthesized, for example, by a production method that includes obtaining (meth)acryloyloxy group-containing compounds represented by the general formula (19) from hydroxyl group-containing compounds represented by the general formula (3). Specifically, the compounds represented by the general formula (19) can be synthesized as in Synthesis Examples 14 and 15 that will be described later.

Compounds represented by the general formula (19) can be synthesized, for example, by reacting hydroxyl group-containing compounds represented by the general formula (3) with (meth)acrylating agents. Examples of (meth)acrylating agents may include (meth)acryloyl halides such as (meth)acryloyl chloride; and (meth)acrylic acid anhydrides. More preferred are (meth)acryloyl halides. More preferred are (meth)acryloyl chlorides. Examples of the reaction temperature may include a temperature of −20 to 150° C., preferably −10 to 100° C., and more preferably 0 to 60° C. The term "(meth)acrylating agent" as used herein refers to both acrylating agents and methacrylating agents, and the term "(meth)acryluic acid a hydride" refers to both acrylic anhydride and methacrylic anhydride.

Compounds represented by the general formula (19) may be purified after the synthesis. The purification method is not limited in particular; and examples thereof may include publicly known methods such as silica gel column chromatography. The purification can result in an improvement in purity of compounds represented by the general formula (19) and a reduction in content of the metallic component. The use of purified compounds is likely to contribute to an improvement in reactivity and, at the same time, can contribute to effective suppression of coloring during the reaction.

<<Transparent Body>>

The transparent body according to the present invention is one produced by the above production method. As described above, the transparent body may be obtained as a transparent film or a transparent molded product by film formation or molding as described above.

The transparent body according to the present invention is excellent in optical properties such as contrast ratio, light transmittance, and refractive index and thermal properties such as heat resistance. The transparent body according to the present invention can be used, for example, in lenses (for example, microlenses), optical members such as optical fibers, light waveguides, prism sheets, holograms, high refractive index films, and retroreflection films; alignment films and flattening films (for example, alignment films and flattening films used, for example, in liquid crystal displays and organic EL displays); resist underlying films such as antireflection films, interlayer insulating films, and carbon hard masks; and semiconductor materials. Further, the transparent body according to the present invention can also be used in display devices such as liquid crystal displays and organic EL displays. Among others, applications where excellent optical properties are required are particularly suitable.

<<Amorphous Body>>

The amorphous body according to the present invention is an amorphous body containing a vinyl-group-containing compound represented by the general formula (1). The amorphous body is composed of a disordered molecular alignment, and does not have distinguishable crystal lattices. The amorphous body is visible as a transparent glassy solid. Specifically, the amorphous body may be the above transparent body or alternatively may be an amorphous body of the vinyl-group-containing compound represented by the general formula (1).

The amorphous body does not exhibit a diffraction peak at a diffraction angle (2θ) of 15.5° to 18.4° in X-ray diffraction measurement (XRD) using a CuKα spectrum.

Specifically, in FIG. 1 that will be described later, the amorphous body does not exhibit a diffraction angle (2θ) of 15.5° to 18.4° as seen in an X-ray diffraction pattern of a transparent film 2 in Comparative Example 1. The diffraction peak at a diffraction angle (2θ) of 15.5° to 18.4°, when the vinyl-group-containing compound represented by the general formula (1) is crystalline, is a characteristic diffraction peak attributable to a regular spacial configuration of the compound constituting the crystal lattice. Accordingly, the amorphous body is preferably a solid obtained by the above production method and is amorphous because the solid does not exhibit a crystal-derived diffraction peak. SmartLab (a name of an apparatus manufactured by Rigaku Corporation) may be used for the X-ray diffraction measurement. The measurement is carried out under conditions of a CuKα line, an incident angle of 0.5° (fixed) and 2θ scan.

The amorphous body does not have an endothermic peak at 100° C. to 200° C. in differential scanning calorimetric measurement (DSC). Specifically, in FIG. 3 that will be described later, the amorphous body does not exhibit an endothermic peak at 100° C. to 200° C. as seen in a DSC curve in Comparative Example 3. The endothermic peak at 100° C. to 200° C., when the vinyl-group-containing compound represented by the general formula (1) is amorphous, is a crystal-derived endothermic peak. Accordingly, the amorphous body is preferably a solid obtained by the above production method and is amorphous because the solid does not exhibit a crystal-derived endothermic peak in a DSC curve.

"STA449F1 Jupiter" (a name of an apparatus manufactured by NETZSCH) may be used as a differential scanning calorimetric measurement apparatus. The measurement may be carried out under conditions of a temperature rise of 10 mg of a sample in a nitrogen atmosphere at a rate of 2° C./min.

"STA449F1 Jupiter" (manufactured by NETZSCH) may be used as a thermogravimetric measurement apparatus. The measurement may be carried out under conditions of a temperature rise of 10 mg of a sample in a nitrogen atmosphere at a rate of 2° C./min.

EXAMPLES

Hereinafter, the present invention will be described more specifically with examples, but the scope of the present invention is not limited to these examples.

<Compounds Represented by the General Formula (1)>

Compounds 1 to 3 represented by the following formulae were provided as the compounds represented by the general formula (1).

[Chem. 33]

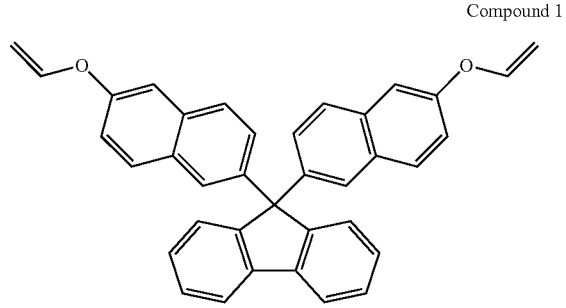

Compound 1

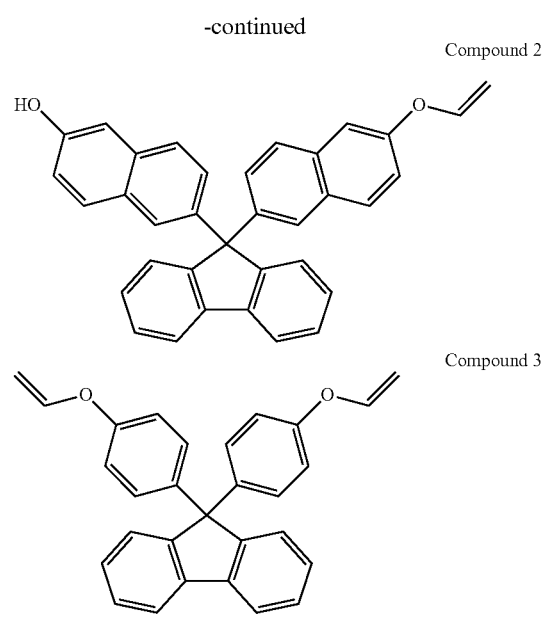

Synthesis methods for Compounds 1 to 3 will be described below (Synthesis Examples 1 to 3). Materials used in Synthesis Examples were as follows.

[Inorganic Base]
(1) Light Ash Sodium Carbonate
Particle diameter distribution: 250 μm or more; 3% by weight 150 μm (inclusive) to 250 μm (exclusive); 15% by weight 75 μm (inclusive) to 150 μm (exclusive); 50% by weight Less than 75 μm; 32% by weight
The particle diameter distribution was calculated by sieving particles with sieves of 60 meshes (250 μm), 100 meshes (150 μm), and 200 meshes (75 μm) and measuring the weight of oversize particles and undersize particles.

[Transition Element Compound Catalyst]
(1) di-μ-chlorobis(1,5-cyclooctadiene)diiridium(I):[Ir(cod)Cl]$_2$

[Hydroxy Compound]
(1) 9,9'-Bis(6-hydroxy-2-naphthyl)fluorene
(2) 9,9'-Bis(4-hydroxyphenyl)fluorene

[Vinyl Ester Compound]
(1) Vinyl propionate

[Synthesis Example 1] Synthesis of Compound 1

A 1000-ml reaction vessel equipped with a cooling pipe and a decanter that conducts separation of a condensate and returns an organic layer to the reaction vessel and discharges a water layer to the outside of the system was charged with di-μ-chlorobis(1,5-cyclooctadiene)diiridium(I)[Ir(cod)Cl]$_2$ (839 mg, 1.25 mmol), light ash sodium carbonate (12.7 g, 0.12 mol), 9,9'-bis(6-hydroxy-2-naphthyl)fluorene (225 g, 0.5 mol), vinyl propionate (125 g, 1.25 mol), and toluene (300 ml). Thereafter, the temperature of the system was gradually raised while stirring with a stirring blade having a surface area of 10 cm$^2$ at a rotation speed of 250 rpm, followed by reflux. A reaction was allowed to proceed for 5 hr under reflux while removing water produced as by-product with the decanter. The reaction solution was analyzed by gas chromatography. As a result, it was found that the conversion of 9,9'-bis(6-hydroxy-2-naphthyl)fluorene was 100%, and 9,9'-bis(6-vinyloxy-2-naphthyl)fluorene (Compound 1) and bis-6-naphtholfluorene monovinyl ether were produced at yields of 81% and 4%, respectively, based on 9,9'-bis(6-hydroxy-2-naphthyl)fluorene.

$^1$H-NMR (CDCl$_3$): 4.47 (dd, 2H, J=1.5 Hz, 5.0 Hz), 4.81 (dd, 2H, J=3.5 Hz, 12.0 Hz), 6.71 (dd, 2H, J=6.0 Hz), 7.12-7.82 (m, 20H)

[Synthesis Example 2] Synthesis of Compound 2 (Isolation)

The reaction product obtained in Synthesis Example 1 was subjected to separation and purification by silica gel column chromatography to isolate bis-6-naphtholfluorene monovinyl ether (Compound 2).

$^1$H-NMR (CDCl$_3$): 4.55 (dd, 1H, J=6.0 Hz), 4.88 (dd, 1H, J=3.5 Hz), 6.79 (dd, 1H, J=6.0 Hz, 14.0 Hz), 7.20-7.89 (m, 20H)

[Synthesis Example 3] Synthesis of Compound 3

A 1000-ml reaction vessel equipped with a cooling pipe and a decanter that conducts separation of a condensate and returns an organic layer to the reaction vessel and discharges a water layer to the outside of the system was charged with di-µ-chlorobis(1,5-cyclooctadiene)diiridium(I) [Ir(cod)Cl]$_2$ (839 mg, 1.25 mmol), light ash sodium carbonate (12.7 g, 0.12 mol), 9,9'-bis(4-hydroxyphenyl)fluorene (186 g, 0.5 mol), vinyl propionate (125 g, 1.25 mol), and toluene (300 ml). Thereafter, the temperature of the system was gradually raised while stirring with a stirring blade having a surface area of 10 cm$^2$ at a rotation speed of 250 rpm, followed by reflux. A reaction was allowed to proceed for 5 hr under reflux while removing water produced as by-product with the decanter. The reaction solution was analyzed by gas chromatography. As a result, it was found that the conversion of 9,9'-bis(4-hydroxyphenyl)fluorene was 100%, and 9,9'-bis(4-vinyloxyphenyl)fluorene (Compound 3) and bis-4-phenolfluorene monovinyl ether were produced at yields of 72% and 9%, respectively, based on 9,9'-bis(4-hydroxyphenyl)fluorene.

$^1$H-NMR (CDCl$_3$): 4.47 (dd, 2H), 4.81 (dd, 2H), 6.71 (dd, 2H), 7.12-7.82 (m, 16H)

Synthesis Examples Through Leaving Group-Containing Compounds Leaving Group-Containing Compounds Synthesis Example 4

6,6'-(9-Fluorenylidene)-bis(2-naphthyloxyethanol) (598 g, 1.11 mol), pyridine (87.8 g, 1.11 mol), and dipropylene glycol dimethyl ether (1670 mL) were added to a 5-L reactor, the atmosphere of the system was replaced by nitrogen, and the temperature was raised to 60° C. Thionyl chloride (395.9 g, 3.33 mol) was added dropwise over a time period of 3 hr, followed by ripening for 2 hr. The reaction solution was cooled to 30° C., water was added to stop the reaction, and methanol was added dropwise at a temperature in the range of 15 to 20° C. to obtain a target compound with the hydroxyl group replaced by chlorine at a yield of 96% (compound represented by the following formula; the compound is referred to also as Compound 4).

$^1$H-NMR (CDCl$_3$): 3.85 (t, 4H, J=6.0 Hz), 4.31 (t, 4H, J=6.0 Hz), 7.08-7.82 (m, 20H)

[Chem. 34]

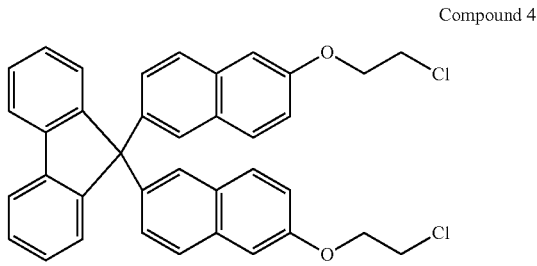

Compound 4

Synthesis Example 5

A solution of potassium-t-butoxide (327.5 g, 2.92 mol) in tetrahydrofuran (1260 mL) was added dropwise at a temperature in the range of 20° C. to 40° C. to a 5-L reactor that had been charged with Compound 4 (560 g, 0.97 mol) and tetrahydrofuran (1260 mL). The reaction solution was ripened at 60° C. for 2 hr. Water was added to stop the reaction. The organic layer was separated and concentrated in an evaporator to a weight that was twice larger than the charged amount of Compound 4. The concentrate was added dropwise to methanol to obtain 9,9'-bis(6-vinyloxy-2-naphthyl)fluorene (compound represented by the following formula, that is, Compound 1) as a white or grayish white solid at a yield of 77%.

$^1$H-NMR (CDCl$_3$): 4.48 (dd, 2H, J=1.5 Hz, 6.5 Hz), 4.81 (dd, 2H, J=1.5 Hz, 13.5 Hz), 6.73 (dd, 2H, J=6.5 Hz, 13.5 Hz), 7.13-7.83 (m, 20H)

[Chem. 35]

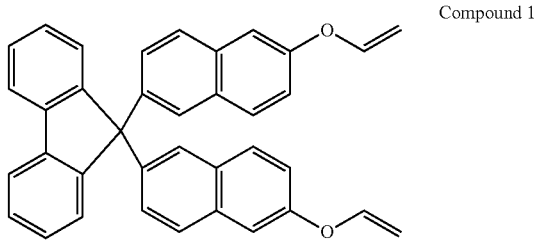

Compound 1

Synthesis Example 6

Ethylene glycol (1.00 g, 0.0161 mol), triethylamine (3.42 g, 0.0338 mol), and tetrahydrofuran (3.38 mL) were added to a 25-mL reactor. The atmosphere of the reactor was replaced by nitrogen, and the system was cooled to 0° C. Methanesulfonyl chloride (3.88 g, 0.0338 mol) was added dropwise over a time period of 2 hr. The reaction solution was ripened for one hr, and water was added to stop the reaction. Ethyl acetate was added, the organic layer was separated, and the solvent was removed by evaporation in an evaporator to obtain a compound that was ethylene glycol at a yield of 80% with a methanesulfonyl group added thereto (compound represented by the following formula; hereinafter referred to also as "EG-DMs").

$^1$H-NMR (CDCl$_3$): 3.10 (s, 6H), 4.47 (s, 4H)

[Chem. 36]

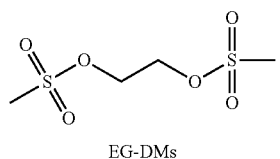

EG-DMs

Synthesis Example 7

6,6-(9-Fluorenylidene)-2,2-dinaphthol (compound represented by the following formula indicated on the left side; 1.00 g, 0.0022 mol; hereinafter referred to also as "Compound 5"), potassium carbonate (0.64 g, 0.0047 mol), and tetrahydrofuran (3.38 mL) were added to a 25-mL reactor. The atmosphere of the reactor was replaced by nitrogen. A solution of EG-DMs (1.02 g, 0.0047 mol) synthesized in Synthesis Example 6 in tetrahydrofuran (1.12 mL) was added at room temperature, the mixture was heated to 60° C., and the reaction solution was ripened for 15 hr. The reaction solution was analyzed by HPLC. As a result, it was found that Compound 6 (compound represented by the following formula indicated on the right side) was synthesized at a conversion of Compound 5 of 99% and a selectivity of 65%.

(Compound 6) $^1$H-NMR (CDCl$_3$): 3.08 (s, 6H), 4.32 (t, 4H, J=4.4 Hz), 4.60 (t, 4H, J=4.4 Hz), 7.05-7.83 (m, 20H)

[Chem. 37]

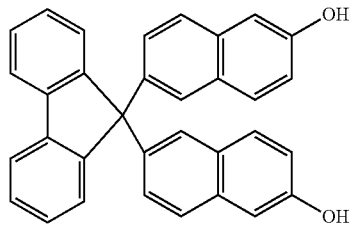

Compound 5

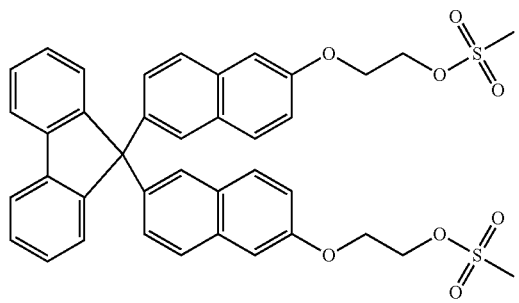

Compound 6 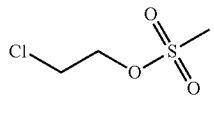

Synthesis Example 8

A solution of potassium-t-butoxide (1.45 g, 0.0130 mol) in tetrahydrofuran (2.25 mL) was added dropwise at a temperature in the range of 20° C. to 40° C. to a 25-mL reactor charged with Compound 6 (2.00 g, 0.00288 mol), dipropylene glycol dimethyl ether (2.25 mL). The reaction solution was ripened at 100° C. for 2 hr. The reaction solution was analyzed by HPLC. As a result, it was found that Compound 1 was synthesized at a conversion of Compound 6 of 99% and a selectivity of 58% and a monovinyl monomesyl compound (compound represented by the following formula; hereinafter referred to also as "Compound 7") was synthesized at a selectivity of 32%.

$^1$H-NMR (CDCl$_3$): 3.10 (s, 3H), 4.34 (t, 2H, J=3.6 Hz), 4.49 (dd, 1H, J=1.2 Hz, 5.2 Hz), 4.62 (t, 2H, J=3.6 Hz), 4.81 (dd, 1H, J=1.2 Hz, 11.2 Hz), 6.73 (dd, 1H, J=5.2 Hz, 11.2 Hz), 7.06-7.83 (m, 20H)

[Chem. 38]

Compound 7

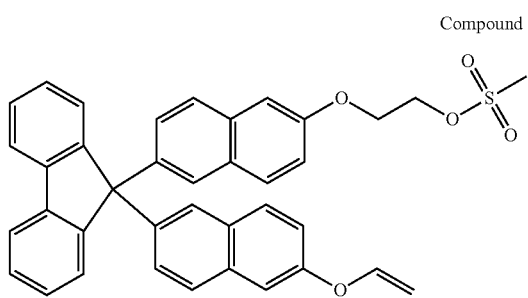

Synthesis Example 9

2-Chloroethanol (3.00 g, 0.048 mol), triethylamine (5.87 g, 0.058 mol), and tetrahydrofuran (10.12 mL) were added to a 50-mL reactor. The atmosphere in the reactor was replaced by nitrogen. Thereafter, the reaction solution was cooled to 0° C. Methanesulfonyl chloride (6.09 g, 0.053 mol) was added dropwise over a time period of 2 hr. The reaction solution was ripened for one hr. Water was added to stop the reaction. Ethyl acetate was added, the organic layer was separated, and the solvent was removed by evaporation in an evaporator to obtain a compound that was 2-chloroethanol with a methanesulfonyl group added thereto (compound represented by the following formula; hereinafter referred to also as "ClEMs") at a yield of 80%.

$^1$H-NMR (CDCl$_3$): 3.09 (s, 3H), 3.77 (t, 2H, J=5.5 Hz), 4.45 (t, 2H, J=5.5 Hz)

[Chem. 39]

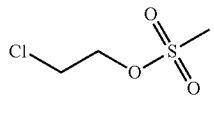

ClEMs

Synthesis Example 10

Compound 5 (1.00 g, 0.0022 mol), potassium carbonate (0.64 g, 0.0047 mol), and dipropylene glycol dimethyl ether (2.23 mL) were added to a 25-mL reactor. The atmosphere in the reactor was replaced by nitrogen. A solution of ClEMs (1.06 g, 0.0067 mol) in dipropylene glycol dimethyl ether (1.12 mL) was added at room temperature. The mixture was heated to 60° C., and the reaction mixture was ripened for 15 hr. The reaction solution was analyzed by HPLC. As a result, it was found that Compound 4 was synthesized at a conversion of Compound 5 of 17% and a selectivity of 4% and Compound 8 (compound represented by the following formula) was synthesized at a selectivity of 12%.

$^1$H-NMR (CDCl$_3$): 3.86 (t, 2H, J=6.0 Hz), 4.32 (t, 2H, J=6.0 Hz), 7.09-7.82 (m, 20H)

[Chem. 40]

Compound 8

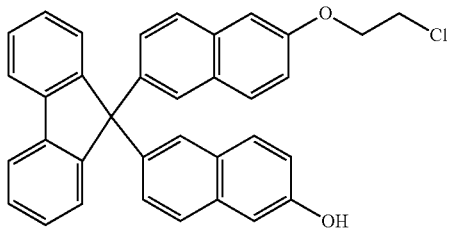

Synthesis Example 11

A solution of potassium-t-butoxide (0.58 g, 0.0052 mol) in tetrahydrofuran (6.8 mL) was added dropwise at a temperature in the range of 20° C. to 40° C. to a 25-mL reactor charged with Compound 4 (3.0 g, 0.0052 mol) and tetrahydrofuran (6.8 mL). The reaction solution was ripened at 60° C. for 2 hr. Water was then added to stop the reaction. The organic layer was analyzed by HPLC. As a result, it was found that Compound 1 was synthesized at a conversion of Compound 4 of 57% and a selectivity of 25% and a monovinyl monochloro compound (compound represented by the following formula; hereinafter referred to also as "Compound 9") was synthesized at a selectivity of 75%.

$^1$H-NMR (CDCl$_3$): 3.84 (t, 2H, J=6.0 Hz), 4.30 (t, 2H, J=6.0 Hz), 4.48 (dd, 1H, J=1.6 Hz, 6.0 Hz), 4.81 (dd, 1H, J=1.6 Hz, 13.6 Hz), 6.72 (dd, 1H, J=6.0 Hz, 13.6 Hz), 7.08-7.82 (m, 20H)

[Chem. 41]

Compound 9

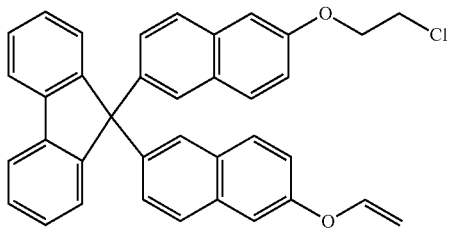

Synthesis Example 12

9,9'-Bis(4-(2-hydroxyethoxy)phenyl)fluorene (6.26 g, 0.0143 mol), pyridine (2.82 g, 0.0357 mol), dipropylene glycol dimethyl ether (33.4 mL), and tetrahydrofuran (33.7 mL) were added to a 200-mL reactor. The atmosphere in the reactor was replaced by nitrogen. The reaction solution was heated to 60° C. Thionyl chloride (6.79 g, 0.0571 mol) was added dropwise over a time period of 2 hr. The reaction solution was then ripened for 2 hr. After cooling to 30° C., water was added to stop the reaction, and methanol was added dropwise at a temperature in the range of 15 to 20° C. to obtain a target compound in which the hydroxyl group was replaced with chlorine (compound represented by the following formula; hereinafter referred to also as "Compound 10") at a yield of 95%.

$^1$H-NMR (CDCl$_3$): 3.75 (t, 4H, J=6.0 Hz), 4.14 (t, 4H, J=6.0 Hz), 6.73-7.75 (m, 16H)

[Chem. 42]

Compound 10

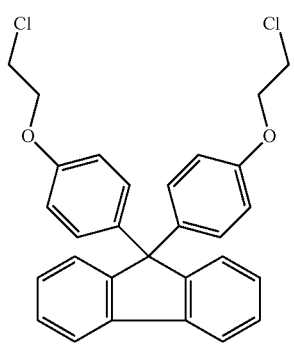

Synthesis Example 13

A solution of potassium-t-butoxide (3.53 g, 0.0315 mol) in tetrahydrofuran (13.6 mL) was added dropwise at a temperature in the range of 20° C. to 40° C. to a 100-mL reactor charged with Compound 10 (5.0 g, 0.0105 mol) and tetrahydrofuran (11.5 mL). The reaction solution was ripened at 60° C. for 2 hr. Water was then added to stop the reaction. The organic layer was separated and concentrated in an evaporator to a weight that was twice larger than the charged amount of Compound 10. The concentrate was added dropwise to methanol to obtain 9,9'-bis(4-vinyloxyphenyl)fluorene (compound represented by the following formula, that is, Compound 3), as a white or grayish white solid at a yield of 79%.

$^1$H-NMR (CDCl$_3$): 4.47 (dd, 2H), 4.81 (dd, 2H), 6.71 (dd, 2H), 7.12-7.82 (m, 16H)

[Chem. 43]

Compound 3

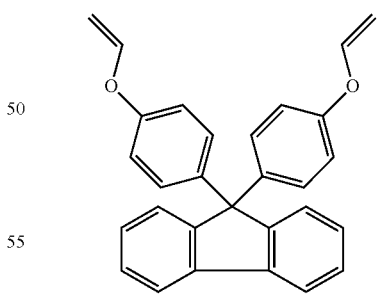

<Compounds Represented by General Formula (19)>

Synthesis Example 14

Compound 5 (3.00 g, 0.00666 mol), triethylamine (1.48 g, 0.0146 mol), phenothiazine (9.00 mg, 0.0000452 mol), and tetrahydrofuran (16.9 mL) were added to a 50-mL reactor. The atmosphere in the reactor was replaced by nitrogen. The reaction solution was cooled to 0° C. Acryloyl chloride (1.51 g, 0.0166 mol) was added dropwise over a time period of one hr, and the reaction solution was ripened for 2 hr. Water was added to stop the reaction, and the organic layer was separated. The solvent was removed by evaporation in an evaporator, and the residue was then purified by silica gel column chromatography to obtain a target diacryl compound (compound represented by the following formula; hereinafter referred to also as "Compound 11") as a white solid at a yield of 63%.

$^1$H-NMR (CDCl$_3$): 6.03 (dd, 2H, J=1.5 Hz, 10.0 Hz), 6.36 (dd, 2H, J=10.0 Hz, 17.5 Hz), 6.63 (dd, 2H, J=1.5 Hz, 17.5 Hz), 7.19-7.84 (m, 20H)

[Chem. 44]

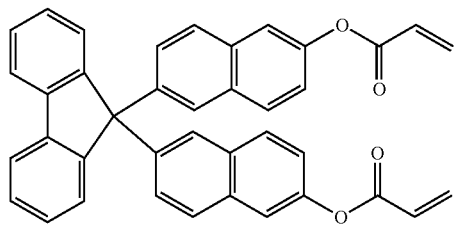

Compound 11

Synthesis Example 15

Compound 5 (3.00 g, 0.00666 mol), triethylamine (1.48 g, 0.0146 mol), phenothiazine (9.00 mg, 0.0000452 mol), and tetrahydrofuran (16.9 mL) were added to a 50-mL reactor. The atmosphere in the reactor was replaced by nitrogen. The reaction solution was then cooled to 0° C. Methacryloyl chloride (1.74 g, 0.0166 mol) was added dropwise over a time period of one hr, and the reaction solution was then gradually heated to 40° C. and ripened for 2 hr. Water was added to stop the reaction, and the organic layer was separated. The solvent was removed by evaporation in an evaporator, and the residue was purified by silica gel column chromatography to obtain a target dimethacryl compound (compound represented by the following formula; hereinafter referred to also as "Compound 12") as a white solid at a yield of 73%.

$^1$H-NMR (CDCl$_3$): 2.08 (s, 6H), 5.77 (s, 2H), 6.38 (s, 2H), 7.18-7.84 (m, 20H)

[Chem. 45]

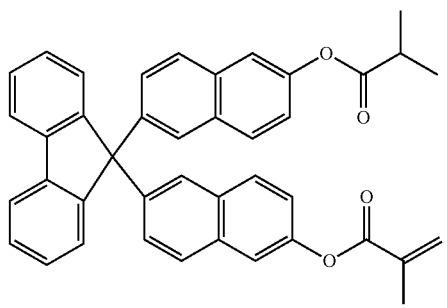

Compound 12

<Purification of Compounds Represented by General Formula (1)>

Compound 1 obtained in Synthesis Example 5 was purified by silica gel column chromatography. The purity of Compound 1 before the purification and the purity of Compound 1 after the purification (proportion of Compound 1 the total of Compound 1 and impurities) were measured by HPLC using an ultraviolet light at 220 nm. Further, the content of a metallic component in Compound 1 before the purification and the content of the metallic component in Compound 1 after the purification were measured by ICP-MS (inductive coupling plasma emission-mass spectroscopic analysis method). The results are shown in Table 1.

[Evaluation]

Each of the Compound 1 before the purification and the Compound 1 after the purification was dissolved in tetrahydrofuran to prepare a 10 mass % solution. The solution was cooled to −30° C. A catalytic amount of boron trifluoride was added to the solution to prepare a reaction solution. The temperature of the reaction solution was raised from −30° C. at a rate of 2° C./min, and a vinyl group reduction start temperature was monitored by infrared spectroscopy to measure the start temperature of a reaction of Compounds 1 itself, followed by evaluation according to the following criteria. The reaction system was visually inspected for coloring. The results are shown in Table 1. Evaluation criteria for reaction start temperature S: The reaction start temperature was 0° C. or below.
A: The reaction start temperature was 0° C. (exclusive) to 20° C. (inclusive)
B: The reaction start temperature was above 20° C.

TABLE 1

|  | Purity (mass %) | Content of metallic component (mass ppm) | | | | | Reaction start temp. | Coloring |
| --- | --- | --- | --- | --- | --- | --- | --- | --- |
|  |  | Na | K | Fe | Cu | Ca |  |  |
| Compound 1 before purification | 92.1 | 500 | 35 | <15 | <15 | <1.5 | B | Yes |
| Compound 1 after purification | 98.5 | <0.05 | <0.1 | <15 | <15 | <1.5 | A | No |

As is apparent from Table 1, as a result of purification by silica gel chromatography, it was confirmed that the Compound 1 had an improved purity and had a reduced metallic component content, particularly a reduced content in sodium component and potassium component. Further, it was confirmed that the purification lowered the start temperature of the reaction of the Compound 1 itself, contributing to an improved reactivity of the Compound 1. Furthermore, it was confirmed that the coloring in the reaction could be suppressed by the purification.

<Production and Evaluation of Transparent Body>

[Measurement of Melting Point]

For Compound 1 after the purification, measurement was carried out with a differential calorimetric/thermogravimetric measurement apparatus (TG/DTA-6200 manufactured by Seiko Instruments Inc under a nitrogen atmosphere to obtain a TG curve and a DTA curve. The melting point of Compound 1 was determined from the DTA curve. As a result, a measurement value of the melting point of Compound 1 was found to be 150° C.

[Production of Transparent Body]

Compound 1 (white powder) after the purification was heated solely (that is, in the absence of a solvent) to 150° C. (that is, a melting point or a temperature above the melting point of Compound 1) for melting. The melt of Compound 1 was coated with a spin coater on a glass substrate, and the coating was cooled to a temperature below the melting point of Compound 1 to obtain a transparent film (thickness 2.0 μm). On the other hand, Compound 1 after the purification (white powder) was dissolved in cyclohexanone to prepare a solution having a concentration of 10% by mass. The solution was coated with a spin coater on a glass substrate, and the coating was baked at 100° C. (that is, a temperature below the melting point of Compound 1) for 120 sec to obtain a transparent film 2 (thickness 2.0 μm). The whole procedure was carried out under a nitrogen atmosphere.

[Evaluation of Contrast Ratio]

For the transparent films 1 and 2 thus obtained, chromaticity coordinates (x, y) in a CIE color system was measured by a C light source in a visual field of 2 degrees with a color analyzer (MCPD2000 manufactured by Otsuka Electronics Co., Ltd.). Further, the glass substrate with the transparent film 1 or 2 formed thereon was held between two deflecting plates. While applying light from a fluorescent lamp (wavelength range 380 to 780 nm) to the assembly from the backside, the deflecting plate on the front side was rotated. The maximum value and the minimum value of the intensity of transmitted light were measured with a luminance meter LS-100 (manufactured by Minolta Co., Ltd.). The maximum value was divided by the minimum value to obtain a contrast ratio. The contrast ratio at a chromaticity coordinate value x=0.650 was determined from the results of measurement. Further, for the glass substrate, the contrast ratio was determined in the same manner as described above. The results are shown in Table 2.

| | Measuring object | Contrast ratio |
|---|---|---|
| Example 1 | Transparent film 1 | 2500 |
| Comparative Example 1 | Transparent film 2 | 3800 |
| Comparative Example 2 | Glass substrate | 4000 |

As is apparent from Table 2, the transparent film 1 had a smaller contrast ratio than the transparent film 2 and the glass substrate. This suggests that, in the transparent film 1, polarization occurs leading to a possibility of a change in crystal state and alignment state.

[Evaluation of Crystal Structure]

Figure 2:
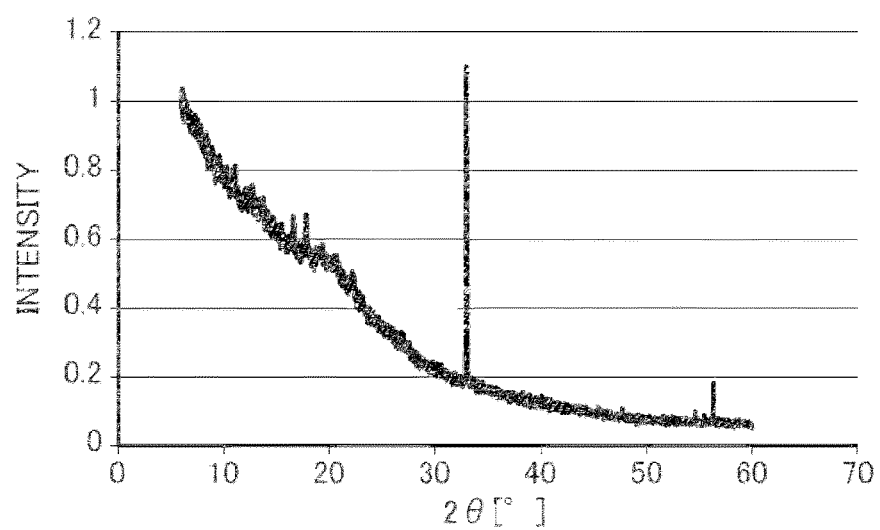
FIG. 2 is a graph illustrating an X-ray diffraction pattern of a transparent film 2 in Comparative Example 1 obtained by X-ray diffraction measurement.

In relation to Example 1 (transparent film 1) and Comparative Example 1 (transparent film 2), an X-ray diffraction analysis (apparatus "SmartLab" manufactured by Rigaku Corporation) was carried out under conditions of a CuKα line, an incident angle of 0.5° (fixed) and 2θ scan. As a result, it was observed that, in Example 1, as illustrated in FIG. 1, characteristic diffraction peaks were not exhibited at 2θ=15.5° to 18.4°. By contrast, for Comparative Example 1, as illustrated in FIG. 2, characteristic peaks appeared at 15.5° to 18.4°. Specifically, characteristic peaks appeared at 15.5° to 17° and 17° to 18.4°, respectively, and peaks having a peak intensity of not less than 0.05 (0.07 ad 0.11, respectively) were observed. From these results, it was found that the transparent film of Example 1 (transparent film 1) was an amorphous body and the transparent film of Comparative Example 1 (transparent film 2) contained crystals. It was confirmed from an X-ray diffraction analysis that was separately carried out for Compound 1 (white powder) (not shown) that the crystal exhibits peaks that are stronger than the peak for the transparent film 2 at 2θ=16.6° and 17.76° (0.72 and 0.92, respectively). From these result, it is estimated that the transparent film 2 is in the form of an aggregate of noncrystalline material and a crystalline material. Here, in the drawing, the highest peaks that appear around diffraction angle 2θ=33° and 56° are peaks derived from a silicon substrate with the transparent film formed thereon. The peak intensity in this evaluation is an intensity ratio when the peak intensity at 2θ=6.02° is presumed to be 1.

Further, for Compound 1 after the purification, differential scanning calorimetric measurement (DSC) and thermogravimetric measurement (TG) were carried out. Specifically, 10 mg of a sample was heated to 200° C. at a temperature rise rate of 2° C./min in a nitrogen atmosphere with "STA449F1 Jupiter" (a name of an apparatus manufactured by NETZSCH) (Comparative Example 3). Thereafter, the same sample was air-cooled to room temperature and was then heated to 300° C.

under the same conditions (Example 2).

Figure 3:
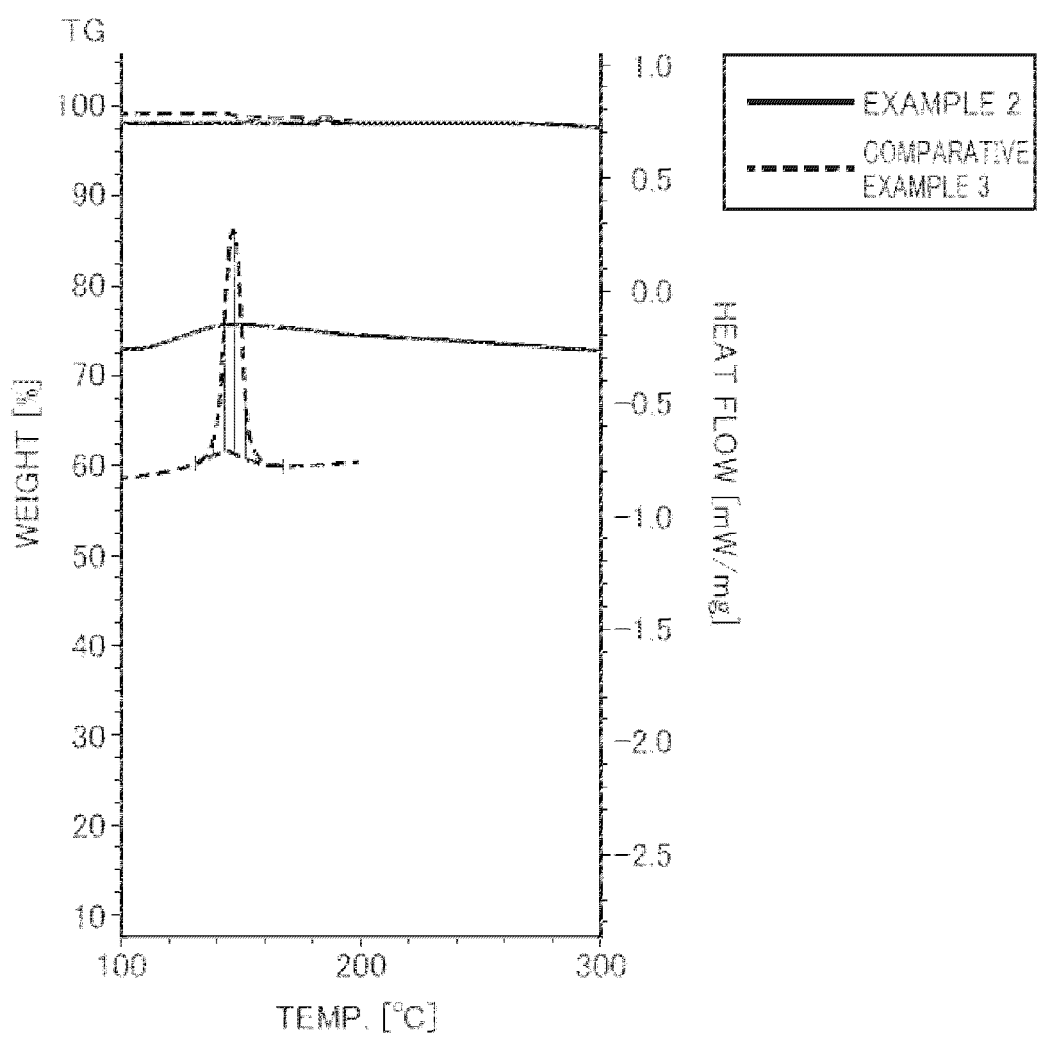
FIG. 3 is a graph illustrating a DSC curve and a TG curve of Example 2 and Comparative Example 3 obtained by differential scanning calorimetric measurement and thermogravimetric measurement.

The results are shown in FIG. 3. In an ordinate in FIG. 3, a peak that goes up toward a positive side is an endothermic peak. For Comparative Example 3, in an initial process of raising the temperature to 200° C., an endothermic peak derived from melting appeared around 149° C. By contrast, in Example 2, after air cooling, in a process of raising the temperature to 300° C., the endothermic peak was not observed. From these results, it was found that a sample that was once heated to the melting point or to a temperature above the melting point had no melting point, indicating that the sample was converted to an amorphous body. Thus, it is suggested that, in Example 2, the transparent body was formed as an amorphous body having no melting point.

The invention claimed is:

1. A method for producing a transparent body, the method comprising heating a compound at or above a melting point of the compound, wherein the compound is solely a vinyl-group-containing compound represented by the following general formula (1):

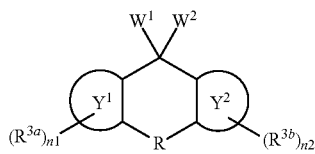

(1)

wherein $W^1$ and $W^2$ are each independently a group having the following general formula (2), a group having the following general formula (4), a hydroxyl group, or a (meth)acryloyloxy group, provided that $W^1$ and $W^2$ are not simultaneously a hydroxyl group or the group having the following general formula (4); a ring $Y^1$ and a ring $Y^2$ are an aromatic hydrocarbon ring which may be the same or different; R is a single bond, an optionally substituted methylene group, an ethylene group that is optionally substituted and may contain a hetero atom between two carbon atoms, —O—, —NH—, or —S—; $R^{3a}$ and $R^{3b}$ are each independently a cyano group, a halogen atom, or a monovalent hydrocarbon group; and n1 and n2 are each independently an integer of 0 to 4,

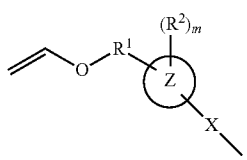

(2)

wherein a ring Z is a fused polycyclic aromatic hydrocarbon ring; X is a single bond or —S—; $R^1$ is a single bond or an alkylene group having 1 to 4 carbon atoms; $R^2$ is a monovalent hydrocarbon group, a hydroxyl group, —$OR^{4a}$, —$SR^{4b}$, an acyl group, an alkoxycarbonyl group, a halogen atom, a nitro group, a cyano group, a mercapto group, a carboxyl group, an amino group, a carbamoyl group, —$NHR^{4c}$, —$N(R^{4d})_2$, a (meth)acryloyloxy group, a sulfo group, or a group formed by substituting at least a part of hydrogen atoms bonded to carbon atoms contained in a monovalent hydrocarbon group, —$OR^{4a}$, —$SR^{4b}$, an acyl group, an alkoxycarbonyl group, —$NHR^{4c}$, or —$N(R^{4d})_2$ with a monovalent hydrocarbon group, a hydroxyl group, —$OR^{4a}$, —$SR^{4b}$, an acyl group, an alkoxycarbonyl group, a halogen atom, a nitro group, a cyano group, a mercapto group, a carboxyl group, an amino group, a carbamoyl group, —$NHR^{4c}$, —$N(R^{4d})_2$, a (meth)acryloyloxy group, a mesyloxy group, or a sulfo group; $R^{4a}$ to $R^{4d}$ are each independently a monovalent hydrocarbon group; and m is an integer of 0 or more, and

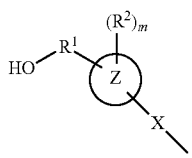

(4)

wherein the ring Z, X, $R^1$, $R^2$, and m are as defined above.

2. The method according to claim 1, wherein the heating is carried out in the absence of oxygen.

3. The method according to claim 1, wherein the ring Z represents a naphthalene ring.

4. The method according to claim 1, wherein $R^1$ represents a single bond.

5. The method according to claim 1, wherein the compound is melted by the heating.

6. A method for producing a transparent body, the method comprising heating a compound at or above a melting point of the compound and melting the compound by the heating, wherein the compound is solely a vinyl-group-containing compound having the following general formula (1):

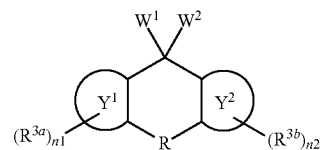

(1)

wherein $W^1$ and $W^2$ are each independently a group having the following general formula (2), a group having the following general formula (4), a hydroxyl group, or a (meth)acryloyloxy group, provided that at least one of W1 and W2 is a group represented by the following general formula (2); a ring $Y^1$ and a ring $Y^2$ are an aromatic hydrocarbon ring which may be the same or different; R is a single bond, an optionally substituted methylene group, an ethylene group that is optionally substituted and may contain a hetero atom between two carbon atoms, —O—, —NH—, or —S—; $R^{3a}$ and $R^{3b}$ are each independently a cyano group, a halogen atom, or a monovalent hydrocarbon group; and n1 and n2 are each independently an integer of 0 to 4,

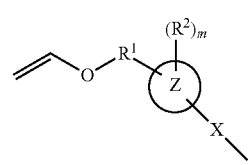

(2)

wherein a ring Z is an aromatic hydrocarbon ring; X is a single bond or —S—; $R^1$ is a single bond or an alkylene group having 1 to 4 carbon atoms; $R^2$ is a monovalent hydrocarbon group, a hydroxyl group, —$OR^{4a}$, —$SR^{4b}$, an acyl group, an alkoxycarbonyl group, a halogen atom, a nitro group, a cyano group, a mercapto group, a carboxyl group, an amino group, a carbamoyl group, —$NHR^{4c}$, —$N(R^{4d})_2$, a (meth)acryloyloxy group, a sulfo group, or a group formed by substituting at least a part of hydrogen atoms bonded to carbon atoms contained in a monovalent hydrocarbon group, —$OR^{4a}$, —$SR^{4b}$, an acyl group, an alkoxycarbonyl group, —$NHR^{4c}$, or —$N(R^{4d})_2$ with a monovalent hydrocarbon group, a hydroxyl group, —$OR^{4a}$, —$SR^{4b}$, an acyl group, an alkoxycarbonyl group, a halogen atom, a nitro group, a cyano group, a mercapto group, a carboxyl group, an amino group, a carbamoyl group, —$NHR^{4c}$, —$N(R^{4d})_2$, a (meth)acryloyloxy group, a mesyloxy group, or a sulfo group; $R^{4a}$ to $R^{4d}$ are each independently a monovalent hydrocarbon group; and m is an integer of 0 or more, and

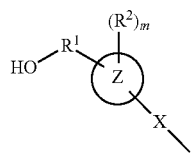  (4)

wherein a ring Z, X, $R^1$, $R^2$, and m are as defined above.

7. The method according to claim 6, wherein the heating is carried out in the absence of oxygen.

8. The method according to claim 6, wherein the ring Z represents a benzene ring or a naphthalene ring.

9. The method according to claim 6, wherein $R^1$ represents a single bond.

10. The method according to claim 6, wherein the ring Z represents a fused polycyclic aromatic hydrocarbon ring in the general formula (2).

11. A method for producing a transparent body, the method consisting essentially of heating a vinyl-group-containing compound at or above a melting point of the compound and melting the compound by the heating, the compound having the following general formula (1); and either:
cooling the compound melted by the heating to a temperature at or below the melting point of the compound for solidification so as to obtain the transparent body; or
further heating the compound melted by the heating for curing so as to obtain the transparent body,

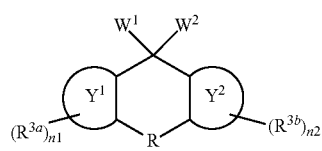  (1)

wherein $W^1$ and $W^2$ are each independently a group having the following general formula (2), a group having the following general formula (4), a hydroxyl group, or a (meth)acryloyloxy group, provided that at least one of $W^1$ and $W^2$ is a group represented by the following general formula (2); a ring $Y^1$ and a ring $Y^2$ are an aromatic hydrocarbon ring which may be the same or different; R is a single bond, an optionally substituted methylene group, an ethylene group that is optionally substituted and may contain a hetero atom between two carbon atoms, —O—, —NH—, or —S—; $R^{3a}$ and $R^{3b}$ are each independently a cyano group, a halogen atom, or a monovalent hydrocarbon group; and n1 and n2 are each independently an integer of 0 to 4,

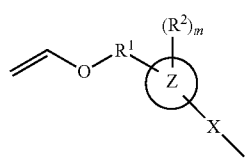  (2)

wherein a ring Z is an aromatic hydrocarbon ring; X is a single bond or —S—; $R^1$ is a single bond or an alkylene group having 1 to 4 carbon atoms; $R^2$ is a monovalent hydrocarbon group, a hydroxyl group, —$OR^{4a}$, —$SR^{4b}$, an acyl group, an alkoxycarbonyl group, a halogen atom, a nitro group, a cyano group, a mercapto group, a carboxyl group, an amino group, a carbamoyl group, —$NHR^{4c}$, —$N(R^{4d})_2$, a (meth)acryloyloxy group, a sulfo group, or a group formed by substituting at least a part of hydrogen atoms bonded to carbon atoms contained in a monovalent hydrocarbon group, —$OR^{4a}$, —$SR^{4b}$, an acyl group, an alkoxycarbonyl group, —$NHR^{4c}$, or —$N(R^{4d})_2$ with a monovalent hydrocarbon group, a hydroxyl group, —$OR^{4a}$, —$SR^{4b}$, an acyl group, an alkoxycarbonyl group, a halogen atom, a nitro group, a cyano group, a mercapto group, a carboxyl group, an amino group, a carbamoyl group, —$NHR^{4c}$, —$N(R^{4d})_2$, a (meth)acryloyloxy group, a mesyloxy group, or a sulfo group; $R^{4a}$ to $R^{4d}$ are each independently a monovalent hydrocarbon group; and m is an integer of 0 or more, and

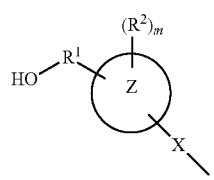  (4)

wherein the ring Z, X, $R^1$, $R^2$, and m are as defined above.

12. The method for producing a transparent body according to claim 1, wherein the transparent body is an amorphous body.

13. The method for producing a transparent body according to claim 6, wherein the transparent body is an amorphous body.

14. The method for producing a transparent body according to claim 11, wherein the transparent body is an amorphous body.

15. The method according to claim 1, wherein at least one of $W^1$ and $W^2$ is a group represented by general formula (2).

16. The method according to claim 1, wherein the compound is represented by the following formula

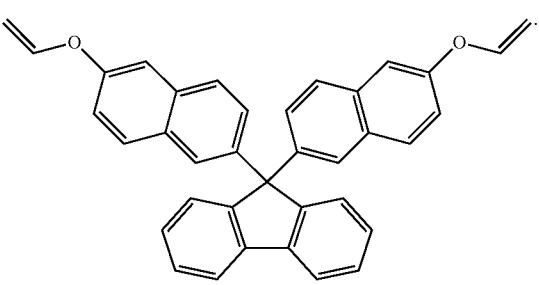 [SMILES: C=COc1ccc2cc(C3(c4ccc5cc(OC=C)ccc5c4)c4ccccc4-c4ccccc43)ccc2c1]

* * * * *